United States Patent [19]
Kawai et al.

[11] Patent Number: 6,121,257
[45] Date of Patent: Sep. 19, 2000

[54] SULFAMATE CONTAINING MACROCYCLIC IMMUNOMODULATORS

[75] Inventors: Megumi Kawai; Indrani W. Gunawardana, both of Libertyville, Ill.

[73] Assignee: Abbott Laboratories, Abbott Park, Ill.

[21] Appl. No.: 09/282,686

[22] Filed: Mar. 31, 1999

[51] Int. Cl.[7] .................... C07D 491/16; A61K 31/445; A61K 31/395

[52] U.S. Cl. .................. 514/214; 514/291; 514/411; 540/456

[58] Field of Search ............................ 540/456; 514/214, 514/291, 411

[56] References Cited

U.S. PATENT DOCUMENTS

| | | | |
|---|---|---|---|
| 3,244,592 | 4/1966 | Arai et al. ................................. | 167/65 |
| 5,877,205 | 3/1999 | Andersson ............................... | 514/449 |

FOREIGN PATENT DOCUMENTS

| | | |
|---|---|---|
| 0184162 | 11/1986 | European Pat. Off. . |
| 0323865 | 12/1989 | European Pat. Off. . |
| WO 94/21642 | 9/1994 | WIPO . |

*Primary Examiner*—Mukund J. Shah
*Assistant Examiner*—Bruck Kifle
*Attorney, Agent, or Firm*—Gregory W. Steele; Robert A. Miller

[57] ABSTRACT

The present invention relates to novel compounds of formula I:

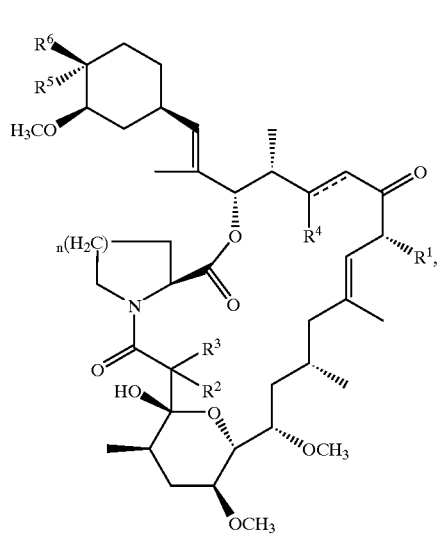

which are useful as immunomodulators, in particular, macrolide immunosuppressants. The invention also relates to the preparation of compounds of formula I, compositions containing such compounds, and methods of using such compounds.

19 Claims, No Drawings

SULFAMATE CONTAINING MACROCYCLIC IMMUNOMODULATORS

FIELD OF THE INVENTION

The present invention relates to novel chemical compounds having immunomodulatory activity, and in particular to macrolide immunosuppressants. More particularly, the invention relates to semisynthetic analogs of ascomycin and FK-506, means for their preparation, pharmaceutical compositions containing such compounds and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Unsatisfactory side-effects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et al., in European Patent Application No. 184162, published Jun, 11, 1986, disclosed a number of macrocyclic compounds isolated from the genus Streptomyces. Immunosuppressant FK-506, isolated from a strain of S. tsukubaensis, is a 23-membered macrocyclic lactone (1a, FIG. 1). Other related natural products, such as FR-900520 (1b, FIG. 1) and FR-900523 (1c, FIG. 1) which differ from FK-506 in their alkyl substituent at C-17 (FIG. 1), have been isolated from S. hygroscopicus yakushimnaensis. Yet another analog, FR-900525 (1d, FIG. 1), produced by S. tsukubaensis, differs from FK-506 by the replacement of the piperdine moiety with a pyrrolidine moiety.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, described the use of ascomycin as an immunosuppressant in European Patent Application No. 323865, published Jul. 12, 1989.

Although the immunosuppressive activity of FK-506 has been clinically confirmed, toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

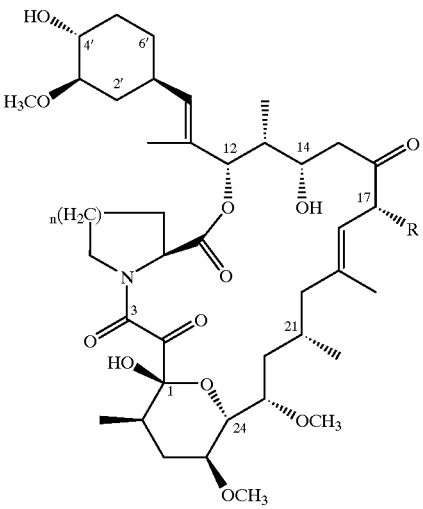

|  |  |  |  |
|---|---|---|---|
| (1a): | FK-506 | R = $CH_2CH\!=\!CH_2$; | n = 2 |
| (1b): | FR-900520 | R = $CH_2CH_3$; | n = 2 |
| (1c): | FR-900523 | R = $CH_3$; | n = 2 |
| (1d): | FR-900525 | R = $CH_2CH\!=\!CH_2$; | n = 1 |

FIG. 1

Fermentation products of FK-type compounds include C-17-epi derivatives of FK-506; a 3'-demethylated derivative of FK-506; 3'-oxo-FK-506 ; compounds derived from FK-506, FR-900523 and FR-900525 which are characterized by the introduction of hydroxy protecting groups; formation of a double bond by elimination of water between carbons 14 and 15; oxidation of the hydroxy group at carbon 14 to the ketone, and reduction of the allyl side-chain at carbon 17 via hydrogenation (FIG. 1). Other published derivatives include those derived from FK-506 and FR-900520 where the lactone ring is contracted to give a macrocyclic ring containing two fewer carbons.

Several microbial transformations of FK-type compounds have been published, such as the microbial demethylation of FR-900520 to form the bis-demethylated 3',25-dihydroxy ring-rearranged derivative of FR-900520; the microbial monodemethylation at carbon 25 of FK-506 and FR-900520; and the microbial monodemethylation of FR-900520 at C-3' (FIG. 1), as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether formation at C-4' and/or C-14, oxidation of C-4' alcohol to the ketone, and epoxide formation at C-2 (FIG. 1).

Although some of these modified compounds exhibit immunosuppressive activity, the need remains for macrocyclic immunosuppressants which do not have the serious side effects frequently associated with immunosuppressant therapy. Accordingly, one object of the present invention is to provide novel semisynthetic macrolides which possess the desired immunomodulatory activity but which may be found to minimize unwanted side effects. More particularly, the present invention provides novel semisynthetic macrolides which bear a sulfamate moiety at C-4' (FIG. 1).

Another object of the present invention is to provide synthetic processes for the preparation of such compounds from starting materials obtained by fermentation, as well as chemical intermediates useful in such synthetic processes.

A further object of the present invention is to provide pharmaceutical compositions containing, as an active ingredient, one of the above compounds. Yet another object of the invention is to provide a method of treating a variety of disease states, including post-transplant tissue rejection and autoimmune dysfunction.

SUMMARY OF THE INVENTION

In one aspect of the present invention are disclosed compounds having formula I:

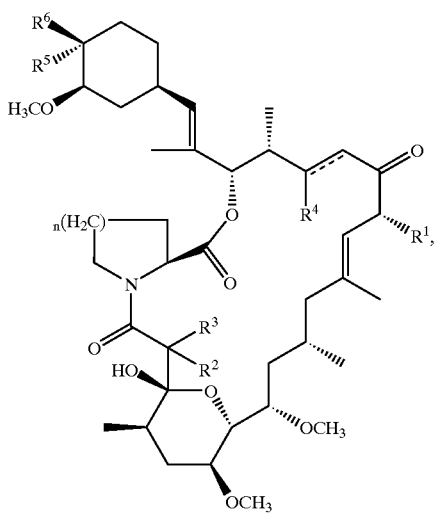

or a pharmaceutically acceptable salt, ester, amide or prodrug thereof, wherein n is an integer of 1–3;

$R^1$ is selected from the group consisting of
  (1) methyl,
  (2) ethyl,
  (3) propyl, and
  (4) allyl;

$R^2$ and $R^3$ are independently selected from the group consisting of
  (1) hydrogen and
  (2) —$OR^7$, wherein $R^7$ is selected from the group consisting of
  a) hydrogen and
  b) hydroxy protecting group or
$R^2$ and $R^3$ taken together are selected from the group consisting of
  (1) oxo and
  (2) thioxo;

$R^4$ is selected from the group consisting of
  (1) hydrogen and
  (2) —$OR^7$, wherein $R^7$ is previously defined;

$R^5$ and $R^6$ are independently selected from the group consisting of
  (1) hydrogen and
  (2) —$OS(O)_2NHR^8$, wherein $R^8$ is selected from the group consisting of
  (a) hydrogen and
  (b) —$C(O)OR^9$, wherein $R^9$ is selected from the group consisting of (i) alkyl,
  (ii) aryl,
  (iii) arylalkyl,
  (iv) cycloalkyl,
  (v) cycloalkylalkyl, and
  (vi) heterocyclealkyl, provided that at least one of $R^5$ and $R^6$ is other than hydrogen; and a broken line represents the presence of an optional double bond, provided that when $R^4$ is —$OR^7$, wherein $R^7$ is hydrogen, the double bond is absent.

In a further aspect of the present invention are disclosed pharmaceutical compositions which comprise a compound of formula I in combination with a pharmaceutically acceptable carrier alone or in combination with another compound of formula I.

In yet another aspect of the present invention is disclosed a method for suppressing the immune system of a mammal comprising administering to the mammal a therapeutically effective amount of a compound of formula I.

In yet another aspect of the present invention is disclosed a method for treating or preventing post-transplant organ or tissue rejection in a mammal comprising administering to the mammal a therapeutically effective amount of a compound of formula I.

In yet another aspect of the present invention is disclosed a method for treating or preventing autoimmune diseases in a mammal comprising administering to the mammal a therapeutically effective amount of a compound of formula I.

Compounds of this invention include, but are not limited to, (1R,9S,12S,13R,14S,17R,21S,23S,24R,25S,27R)-17-ethyl-1,14-dihydroxy-23,25-dimethoxy-12-{(E)-2-[(1R,3R,4R)-3-methoxy-4-({[(methoxycarbonyl)amino]sulfonyl}oxy)cyclohexyl]-1-methylethenyl}-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-12-{(E)-2-[(1R,3R,4R)-4-({[(ethoxycarbonyl)amino]sulfonyl}oxy)-3-methoxycyclohexyl]-1-methylethenyl}-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-12-((E)-2-{(1R,3R,4R)-4-[({[(benzyloxy)carbonyl]amino}sulfonyl)oxy]-3-methoxycyclohexyl}-1-methylethenyl)-17-ethyl-1, 14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-12-{(E)-2-[(1R,3R,4R)-4-({[(tert-butoxycarbonyl)amino]sulfonyl}oxy)-3-methoxycyclohexyl]-1-methylethenyl}-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-1 8-ene, (1R,9S,12S,13R,14S,17R,21S,23S,24R,25S,27R)-12-((E)-2-{(1R,3R,4R)-4-[({[(cyclopentyloxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-12-((E)-2-{(1R,3R,4R)-4-[({[(cyclohexyloxy)carbonyl]amino}sulfonyl)oxy]-3-methoxycyclohexyl }-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-12-((E)-2-{(1R,3R,4R)-4-[({[(cycloheptyloxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-17-ethyl-1,14-dihydroxy-23,25-dimethoxy-12-((E)-2-{(1R,3R,4R)-3-methoxy-4-[({[(4-pyridinylmethoxy)carbonyl]amino}sulfonyl)oxy]cyclohexyl}-1-methylethenyl)-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-17-ethyl-1,14-dihydroxy-23,25-dimethoxy-12-((E)-2-{(1R,3R,4R)-3-methoxy-4-[({[(3-pyridinylmethoxy)carbonyl]amino}sulfonyl)oxy]cyclohexyl}-1-methylethenyl)-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-17-ethyl-1,14-dihydroxy-23,25-dimethoxy-12-((E)-2-{(1R,3R,4R)-3-methoxy-4-[({[(2-pyridinylmethoxy)carbonyl]amino}sulfonyl)oxy]cyclohexyl}-1-methylethenyl)-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-17-ethyl-1,14-dihydroxy-23,25-dimethoxy-12-[(E)-2-((1R,3R,4R)-3-methoxy-4-{[({[(4-nitrobenzyl)oxy]carbonyl}amino)sulfonyl]oxy}cyclohexyl)-1-methylethenyl]-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-17-ethyl-1,14-dihydroxy-12-{(E)-2-[(1R,3R,4R)-4-({[({[(1R,2S,5R)-2-isopropyl-5-methylcyclohexyl]oxy}carbonyl)amino]sulfonyl}oxy)-3-methoxycyclohexyl]-1-methylethenyl}-23,25-dimethoxy-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-12-((E)-2-{(1R,3R,4R)-4-[({[(1-adamantylmethoxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene, and (1R,2R,4R)-4-{(E)-2-[(1R,9S,12S,13R,14S,17R,21S,23S,24R,25S,27R)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-en-12-yl]-1-propenyl}-2-methoxycyclohexylsulfamate.

DETAILED DESCRIPTION OF THE INVENTION

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

Compounds of the present invention can exist as stereoisomers, wherein asymmetric or chiral centers are present. Stereoisomers are designated "R" or "S," depending on the configuration of substituents around the chiral carbon atom. The terms "R" and "S" used herein are configurations as defined in IUPAC 1974 *Recommendations for Section E, Fundamental Stereochemistry*, Pure Appl. Chem., (1976), 45: 13–30, hereby incorporated by reference. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the present invention were named according to the rules described in *International Union of Pure and Applied Chemistry, Organic Chemistry Division, Commission on Nomenclature of Organic Chemistry, Nomenclature of Organic Chemistry*, Sections A, B, C, D, E, F, and H, 1979 edition, J. Rigaudy and S. P. Klesney, eds, Pergamon Press, Oxford, (1979) (Sections A, B, and C) and *International Union of Pure and Applied Chemistry, Organic Chemistry Division, Commission on Nomenclature of Organic Chemistry, A Guide to IUPAC Nomenclature of Organic Compounds*, Recommendations 1993, Blackwell Science, 1993.

Definition of Terms

As used throughout this specification and in the appended claims, the following terms have the meanings specified:

The term "alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkyl," as used herein, refers to a straight or branched chain hydrocarbon containing from 1-to-6 carbon atoms. Representative examples of alkyl include, but are not limited to, methyl, ethyl, n-propyl, iso-propyl, n-butyl, sec-butyl, iso-butyl, tert-butyl, n-pentyl, n-hexyl, and the like.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonyloxy," as used herein, refers to an alkylcarbonyl group, as defined herein, appended to the parent molecular moiety through an oxy group, as defined herein. Representative examples of alkylcarbonyloxy include, but are not limited to, acetyloxy, ethylcarbonyloxy, tert-butylcarbonyloxy, and the like.

The term "alkylene" denotes a divalent group derived from a straight or branched chain hydrocarbon of from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH$_2$CH(CH$_3$)CH$_2$—, and the like.

The term "alkylthio," as used herein, refers to an alkyl group, as defined herein, appended to the parent molecular moiety through a thio group, as defined herein. Representative examples of alkylthio include, but are not limited, methylthio, ethylthio, tert-butylthio, hexylthio, and the like.

The term "allyl," as used herein, refers to a —CH$_2$CH=CH$_2$ group.

The term "amido" as used herein, refers to a —C(O)NR$^{80}$R$^{81}$ group, wherein R$^{80}$ and R$^{81}$ are independently selected from the group consisting hydrogen, alkyl, aryl, and arylalkyl, as defined herein. Representative examples of —C(O)NR$^{80}$R$^{81}$ include, but are not limited to, aminocarbonyl, dimethylaminocarbonyl, methylaminocarbonyl, diethyarninocarbonyl, benzylaminocarbonyl, and the like.

The term "amino" as used herein, refers to a —NR$^{82}$R$^{83}$ group, wherein R$^{82}$ and R$^{83}$ are independently selected from the group consisting hydrogen, alkoxycarbonyl, alkyl, alkylcarbonyl, aryl, arylalkoxycarbonyl, arylalkyl, and formyl, as defined herein. Representative examples of —NR80R$^{81}$ include, but are not limited to, acetylamino, benzyloxycarbonylamino, formylamino, ethoxycarbonylamino, acetylmethylamino, and the like.

The term "aryl," as used herein, refers to a phenyl group.

The aryl groups of this invention can be substituted with 1, 2, or 3 substituents independently selected from alkoxy, alkoxycarbonyl, alkyl, alkylcarbonyl, alkylcarbonyloxy, alkylthio, amido, amino, carboxy, cyano, ethylenedioxy, formyl, halogen, haloalkyl, hydroxy, methylenedioxy, and nitro.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-phenylpropoxy, 5-phenylpentyloxy, and the like.

The term "arylalkoxycarbonyl," as used herein, refers to an arylalkoxy group, as defined herein, appended to the parent molecular moiety through a carbonyl group, as defined herein. Representative examples of arylalkoxycarbonyl include, but are not limited to, benzyloxycarbonyl, 2-phenylethoxycarbonyl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and the like.

The term "carbonyl," as used herein, refers to a —C(O)— group.

The term "carboxy," as used herein, refers to a —CO$_2$H group.

The term "cyano," as used herein, refers to a —CN group.

The term "cycloalkyl", as used herein, refers to a monocyclic, bicyclic, or tricyclic ring system. Monocyclic ring systems are exemplified by a saturated cyclic hydrocarbon group containing from 3 to 12 carbon atoms. Representative examples of monocyclic ring systems include, but are not limited to, cyclopropyl, cyclobutyl, cyclopentyl, cyclohexyl, cycloheptyl, cyclooctyl, and the like. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, and the like. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane, tricyclo[3.3.1.1$^{3,7}$]decane (adamantane), and the like.

The cycloalkyl groups of this invention can be substituted with 1, 2, or 3 substituents independently selected from alkoxy, alkyl, halogen, haloalkyl, and —OR$^7$.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, adamantylmethyl, and 4-cycloheptylbutyl, and the like.

The term "ethyl," as used herein, refers to a —CH$_2$CH$_3$ group.

The term "ethylenedioxy," as used herein, refers to a —O(CH$_2$)$_2$O— group wherein the oxygen atoms of the ethylenedioxy group are attached to the parent molecular moiety through two adjacent carbon atoms.

The term "formyl," as used herein, refers to a —C(O)H group.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

The term "heterocycle" or "heterocyclic," as used herein, refers to a monocyclic or bicyclic system. Monocyclic ring systems are exemplified by any 5- or 6-membered ring containing a heteroatom independently selected from oxygen, nitrogen and sulfur; or a 5-or 6-membered ring containing one, two or three heteroatoms wherein the heteroatoms are independently selected from nitrogen, oxygen and sulfur. The 5-membered ring has 2 double bonds and the 6-membered ring has 3 double bonds. Representative examples of monocyclic ring systems include, but are not limited to, furan, imidazole, isothiazole, isoxazole, oxadiazole, oxazole, pyrazine, pyrazole, pyridine, pyrimidine, pyridazine, pyrrole, tetrazine, tetrazole, thiadiazole, thiazole, thiophene, triazine, triazole, and the like. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazole, benzthiazole, benzothiophene, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

The heterocycles of this invention can be substituted with 1, 2, or 3 substituents independently selected from alkoxy, alkoxycarbonyl, alkyl, alkylcarbonyl, alkylcarbonyloxy, alkylthio, amido, amino, carboxy, cyano, formyl, halogen, haloalkyl, hydroxy, and nitro.

The term "heterocyclealkyl," as used herein, refers to a heterocycle, as defined herein, appended to the parent molecular moiety through an alkyl group, as defined herein. Representative examples of heterocyclealkyl include, but are not limited to, pyrid-3-ylmethyl, 2-pyrimidin-2-ylpropyl, and the like.

The term "hydroxy," as used herein, refers to an -OH group.

The term "hydroxy protecting group" or "O-protecting group" refers to a substituent which protects hydroxyl groups against undesirable reactions during synthetic or semisynthetic procedures. Examples of hydroxy-protecting groups include, but are not limited to, substituted methyl ethers, for example, methoxymethyl, benzyloxymethyl, 2-methoxyethoxymethyl, 2-(trimethylsiyll)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. H. Greene and P. G. M. Wuts, Protective Groups in Organic Synthesis, 2nd edition, John Wiley & Sons, New York (1991), which is hereby incorporated by reference.

The term "mammal," as used herein, has its ordinary meaning and includes human beings.

The term "methyl," as used herein, refers to a —CH$_3$ group.

The term "nitro," as used herein, refers to a —NO$_2$ group.

The term "oxo," as used herein, refers to (=O).

The term "oxy," as used herein, refers to (—O—).

The term "propyl," as used herein, refers to a —CH$_2$CH$_2$CH$_3$ group.

The term "thio," as used herein, refers to (—S—).

The term "thioxo," as used herein, refers to (=S).

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et al., "Pharmaceutical Salts," *J. Pharm. Sci.*, 66: 1–19 (1977) which is incorporated herein by reference.)

Examples of pharmaceutically acceptable, non-toxic esters of the compounds of this invention include C$_1$ to C$_6$ alkyl esters wherein the alkyl group is a straight or branched chain. Acceptable esters also include C$_5$ to C$_7$ cycloalkyl esters as well as arylalkyl esters such as, but not limited to benzyl. Preferred alkyl esters are C$_1$ to C$_4$. Esters of the compounds of the present invention may be prepared according to conventional methods.

Examples of pharmaceutically acceptable, non-toxic amides of the compounds of this invention include amides derived from ammonia, primary C$_1$ to C$_6$ alkyl amines and secondary C$_1$ to C$_6$ dialkyl amines wherein the alkyl groups are straight or branched chain. In the case of secondary amines the amine may also be in the form of a 5 or 6 membered heterocycle containing one nitrogen atom. Amides derived from ammonia, C$_1$ to C$_3$ alkyl primary amides and C$_1$ to C$_2$ dialkyl secondary amides are preferred. Amides of the compounds of the invention may be prepared according to conventional methods.

The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimede) method, the active ester method (p-nitrophenyl ester method, N-hydroxysuccinic acid imide ester method, cyanomethyl ester method and the like), the Woodward reagent K method, the DCC-HOBT (1-hydroxy-benzotriazole) method and the like. Classical methods for amino acid condensation reactions are described in "Peptide Synthesis" Second Edition, M. Bodansky, Y. S. Klausner and M. A. Ondetti (1976).

Determination of Biological Activity In Vitro Assay of Biological Activity

The immunosuppressant activity of the compounds of the present invention was determined using the human mixed lymphocyte reaction (MLR) assay described by Kino, T. et al., in Transplantation Proceedings, XIX(5):36–39, Suppl. 6 (1987), hereby incorporated by reference. The results of the assay, shown below in Table 1, demonstrate that the compounds of the present invention are effective immunomodulators at sub-micromolar concentrations.

TABLE 1

| Example Number | IC$_{50}$ (nM) |
| --- | --- |
| 1 | 0.73 |
| 2 | 0.57 |
| 3 | 3.96 |
| 4 | 0.99 |
| 5 | 26.08 |
| 6 | 4.7 |
| 7 | 9.63 |
| 8 | 0.10 |
| 9 | 4.77 |
| 10 | 0.16 |
| 11 | 6.68 |
| 12 | 24.53 |
| 13 | 21.57 |
| 14 | 0.82 |

In Vivo Assay of Biological Activity Whole blood concetration in the Rat.

Lewis rats (obtained from Charles River, Wilmington, Mass.), weighing 225–250 grams, were acclimated for one week in a AAALAC approved facility. All animals were fasted overnight prior to dosing and throughout the study period but were permitted free access to water. Groups of animals were given FK-506 or Example 14 at a dose of 5 mg/kg. Drugs were given in a 2 ml/kg volume of 10% ethanol, 40% propylene glycol and 2% cremophore in 5% dextrose solution for both oral (p.o.) and intraperitoneal (i.p.) administration, and in a 1 ml/kg volume of the same vehicle without cremophor for intravenous (i.v.) dosing. Blood samples were collected from the tail vein in heparinized tubes at selected time points 0.25, 2.0, and 4.0 hours after dosing.

Drugs were separated from the hemolyzed whole blood contaminants utilizing liquid-liquid extraction with ethyl acetate:hexane (1:1 by volume). Samples were centrifuged at 1200 x g for 10 minutes (4° C.) and a constant volume of the organic layer was transferred to a conical centrifuge tube and evaporated to dryness with a gentle stream of dry air over low heat (~35° C.). The samples were reconstituted with 40% (v/v) acetonitrile in water with vortexing. The compounds of interest were separated from the co-extracted components by a 5 cm×4.6 mm, 3 µm Spherisorb ODS-2 column (Regis, Morton Grove, Ill.) with an acetonitrile:methanol: 0.1% trifluoroacetic acid/0.01 M tetramethylammonium perchlorate mixture (45:5:50 by volume for FK506, 40:5:55 for analogue Example 14) at a flow rate of 1.0 ml/min with UV detection at 205 nm. The temperature of the HPLC column was maintained at 70° C.

The concentration of each sample in whole blood was calculated by a least squares linear regression analysis of the peak area compared to spiked rat blood standards. The data for whole blood concentration is shown in Table 2.

TABLE 2

| | Whole Blood Concentration (µg/mL) at | | |
| --- | --- | --- | --- |
| Example number | 0.25 hours | 2 hours | 4 hours |
| FK-506 | 1.14 | 0.44 | 0.43 |
| Example 14 | 1.40 | 0.05 | 0.00 |

The data in Table 2 show that Example 14 was rapidly eliminated from the blood after 2 hours. This result suggests that sulfamates of the present invention may have reduced adverse systemic effects and therefore may be an advantage when a topical application is considered.

The compounds of the present invention, including but not limited to those specified in the examples, possess immunomodulatory activity in animals. As immunosuppressants, the compounds of the present invention may be useful for the treatment and prevention of immune-mediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucosa and blood vessels such as gastric ulcers, vascular damage caused by ischemic diseases and thrombosis, ischemic bowel diseases, inflammatory bowel diseases, necrotizing enterocolitis, intestinal lesions associated with thermal bums and leukotriene B$_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g. migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcets disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, anti-inflammatory activity, and so on.

Additionally, some compounds appear to possess FK-506 antagonistic properties. The compounds of the present invention may thus be used in the treatment of immunodepression or a disorder involving immunodepression. Examples of disorders involving immunodepression include AIDS, cancer, senile dementia, trauma (including wound healing, surgery and shock) chronic bacterial infection, and certain central nervous system disorders. The immunodepression to be treated may be caused by an overdose of an immunosuppressive macrocyclic compound, for example derivatives of 12-(2-cyclohexyl-1-methylvinyl)-13,19,21, 27-tetramethyl-11,28-dioxa-4-azatricyclo[22.3.1.0$^{4,9}$] octacos-18-ene such as FK-506, or rapamycin. Overdosing of such medicants by patients is quite common upon their realizing that they have forgotten to take their medication at the prescribed time and can lead to serious side effects.

A further situation in which the compounds of the present invention may be used to treat immunosuppression is in vaccination. It is sometimes found that the antigen introduced into the body for the acquisition of immunity from disease acts as an immunosuppressive agent, and so antibodies are not produced by the body and immunity is not acquired. By introducing a compound of the invention into the body (as in a vaccine), the undesired immunosuppression may be overcome and immunity acquired.

Aqueous liquid compositions of the present invention may be particularly useful for the treatment and prevention of various diseases of the eye such as autoimmune diseases (including, for example, conical cornea, keratitis, dysophia epithelialis comeae, leukoma, Mooren's ulcer, sclevitis and Graves' ophthalmopathy) and rejection of corneal transplantation.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat gastrointestinal disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.001 to about 3 mg/kg/day. For purposes of oral administration, more preferable doses may be in the range of from about 0.005 to about 1.5 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of the invention and a pharmaceutically acceptable carrier or excipient, which may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as automimmue diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

Synthetic Methods

The compounds of the present invention may be prepared using one or more of the processes which follow. The starting materials for use in these processes are preferably one of the macrolides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, USA under the provisions of the Budapest Treaty, under deposit No. NRRL 18488. The macrolide FR-900520 (European Patent Application 0184162), also known as ascomycin, may be prepared in accordance to the published methods of (i) H. Hatanaka, M. Iwami, T. Kino, T. Goto and M. Okuhara, FR-900520 and FR-900523, *Novel immunosuppressants isolated from A streptomyces. I. Taxonomy of the producing strain. J. Antibiot.*, 1988. XLI(11), 1586–1591; (ii) H. Hatanaka, T. Kino, S. Miyata, N. Inamura, A. Kuroda, T. Goto, H. Tanaka and M. Okuhara, FR-900520 and FR-900523, *Novel immunosuppressants isolated from A streptomyces. II. Fermentation, isolation and physico-chemical and biological characteristics. J. Antibiot.*, 1988. XLI(11), 1592–1601; (iii) T. Arai, Y. Koyama, T. Suenaga and H. Honda, *Ascomycin, An Antifungal Antibiotic. J. Antibiot.*, 1962. 15(231–2); and (iv) T. Arai in U.S. Pat. No. 3,244,592. One or more of the processes discussed below may be then employed to produce the desired compound of the invention.

The compounds and processes of the present invention will be better understood in connection with the following synthetic schemes 1–2, which illustrate the methods by which the compounds of the invention can be prepared.

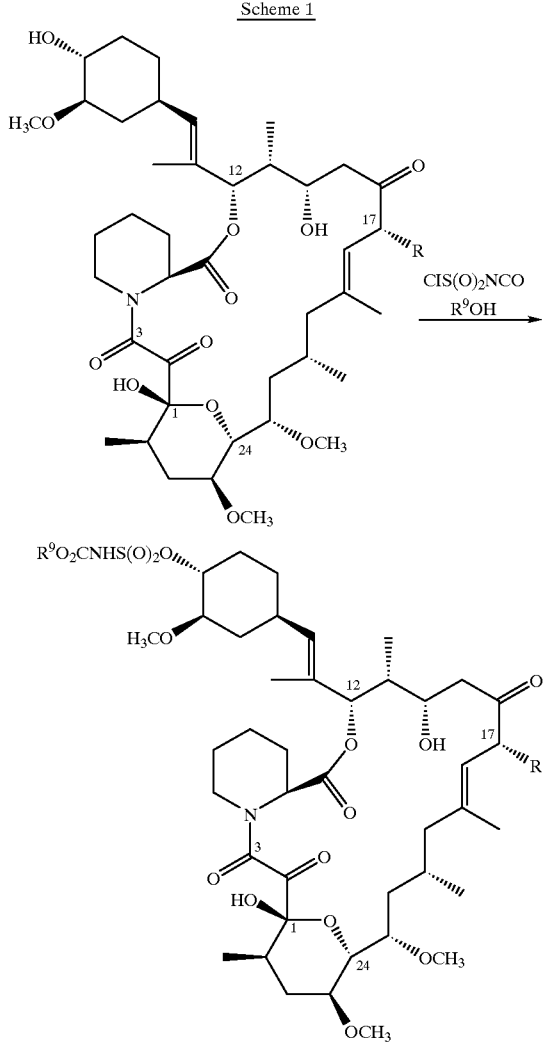

Scheme 1

The chlorosulfane reaction to give the acylsulfamate can be accomplished in a solvent which does not adversely affect the reaction (e.g., benzene, diethylether, dichloromethane, tetrahydrofuran, chloroform or N,N-dimethylformamide or a mixture thereof). The reaction may require cooling or heating, depending on the O-sulfonamidation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, lutidine, picoline, 4-N,N-dimethylaminopyridine, etc.), quinoline, and the like, preferably in the presence of organic bases such as triethylamine, diisopropylethylamine or pyridine.

The reaction temperature is usually conducted from −40° C. to 35° C., preferably from 0° C. to 30° C. The reaction may require 5 minutes to one day, depending on the reagent chosen, preferably from 5 minutes to 2 hours.

Scheme 2

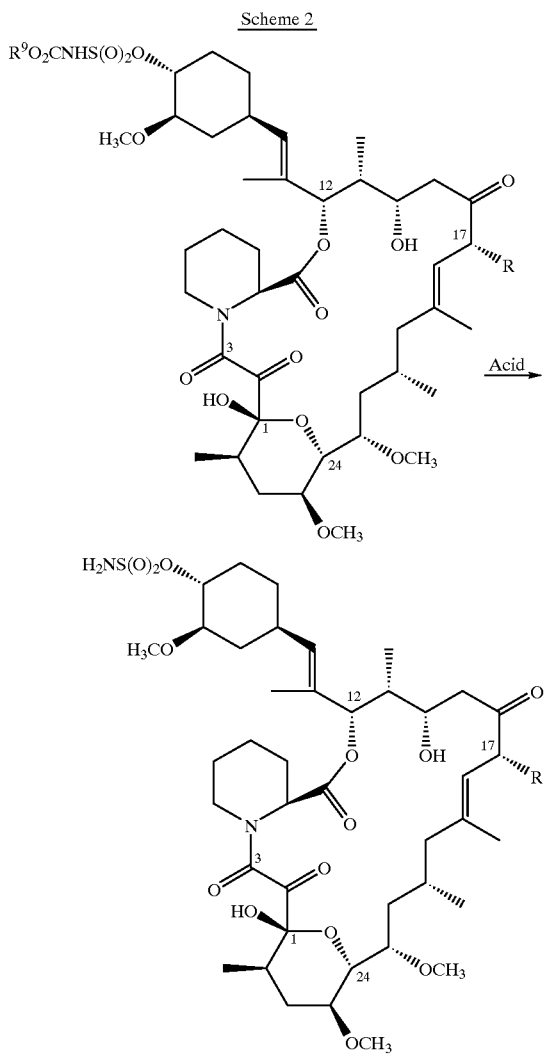

Removal of the acyl group, such as when R⁹ is tert-butyl, to give the sulfamate can be carried out under acidic conditions such as 4N-HCl in dioxane, HCl in ethyl acetate and the like.

The reaction may be carried out in a solvent which does not adversely affect the reaction (e.g., diethylether, dichloromethane, tetrahydrofuran, acetonitrile, benzene, toluene, chloroform or N,N-dimethylformamide or a mixture thereof), preferably dioxane, tetrahydrofuran, ethyl acetate or a mixture thereof. The reaction may require cooling or heating, depending on the method chosen, preferably from 0° C. to 30° C.

In schemes 1–2, the hydroxy group at C-14 position may or may not be necessary to protect. When it is protected, suitable protecting groups for hydroxyl include those groups well known in the art which are: dimethylthexylsilyl, trisubstituted silyl such as tri(lower)alkylsilyl (e.g. trimethylsilyl, triethylsilyl, tributylsilyl, tri-i-propylsilyl, tert-butyldimethylsilyl, tri-tert-butylsilyl, triphenylmethyldimethylsilyl, etc.); lower alkyldiarylsilyl (e.g. methyldiphenylsilyl, ethyl-diphenylsilyl, propyl-diphenylsilyl, tert-butyl-diphenylsilyl, etc.), and the like; triarysilyl (e.g. triphenylsilyl, tri-p-xylylsilyl, etc.); triarylalkylsilyl (e.g. tribenzylsilyl, etc.), and the like, in which the preferred one may be tri($C_1$–$C_4$)alkylsilyl and $C_1$–$C_4$ alkyldiphenylsilyl, and the most preferred one may be tert-butyldimethylsilyl;

Suitable o-silylations may be carried out using a wide variety of organosilicon reagents such as, but not limitted to tert-butyldimethylsilyl chloride, N-(tert-butyldimethylsilyl)-N-methyltrifluoroacetamide (Mawhinney, T., and Madison, M. A. *J. Org. Chem.*, 1982, 47, 3336), tert-butylchlorodiphenylsilane (Hanessian, S. and Lavallee, P *Can. J. Chem.*, 1975, 63, 2975), tert-butyldimethylsilyl trifluoromethanesulfonate (Mander, L. N. and Sethi, S. P. *Tetrahedron Lett.*, 1984, 25, 5953), Dimethylthexylsilyl chloride or Dimethylthexylsilyl trifluoromethanesulfonate (Wetter, H. and Oertle, K. *Tetrahedron Lett.*, 1985, 26, 5515), 1-(tert-butyldimethylsilyl)-imidazole, and the like.

In the process, when the C-14 hydroxy group is protected by the above groups, suitable reagents for deprotection of a protecting group from C-14 may be carefully carried out using, but not limitted to aqueous hydrogen fluoride in acetonitrile (Newton, R. F., Reynolds, D. P., Finch, M. A. W., Kelly, D. R. and Roberts, S. M. *Tetrahedron Lett.*, 1979, 3891), tetraalkyl ammonium fluoride in tetrahydrofuran (Corey, E. J. and Snider, B. B. *J. Am. Chem. Soc.*, 1972, 94, 2549, Corey, E. J. and Venkateswarlu, A. *J. Am. Chem. Soc.*, 1972, 94, 6190) or tetraalkyl ammonium chloride-potassium fluoride in acetonitrile (Carpino, L. A. and Sau, A. C. *J Chem. Soc., Chem. Commun.* 1979, 514) whererin an alkyl group as defined above, p-toluenesulfonic acid, potassium carbonate in anhydrous methanol (Hurst, D. T. and MaInnes, A. G. *Can. J. Chem.*, 1965,43, 2004), citric acid in methanol (Bundy, G. L. and Peterson, D. C. *Tetrahedron Lett.*, 1978, 41), acetic acid: water (3: 1) (Corey, E. J. and Varma, R. K. *J. Am. Chem. Soc.*, 1971, 93, 7319), Dowex 50W-X8 in methanol (Corey, E. J., Ponder, J. W. and Ulrich, P. *Tetrahedron Lett.*, 1980, 21, 137), boron trifluoride etherate in chloroform (Kelly, D. R., Roberts, M. S. and Newton, R. F. *Synth. Commun.* 1979, 9, 295), methanolic hydrogen fluoride (Hanessian, S. and Lavallee, P. *Can. J. Chem.*, 1975, 53, 2975; ibid., 1977, 55, 562), and pyridinuim fluoride in tetrahydrofuran (Nicolaou, K. C., Seitz, S. P., Pavia, M. R. and Petasis, N. A. *J. Org. Chem.*, 1979, 44, 4011); pyridinium p-toluenesulfonate in ethanol (Prakash, C., Saleh, S. and Blair, I. A. *Tetrahedron Lett.*, 1989, 30, 19); N-bromosuccinimide in dimethylsulfoxide (Batten, R. J., Dixon, A. J., Taylor, R. J. K. and Newton, R. F. *Synthesis*, 1980, 234); or Tetraethyldiboroxane in the presence of catalytic amounts of trimethylsilyl triflate (Dahlhoff, W. V. and Taba, K. M. *Synthesis*, 1986, 561) and the like.

The reaction temperature is usually conducted from between –40° C. and 60° C., preferably from 0° C. to 50° C. The reaction may require 20 minutes to one day, depending on the reagent chosen.

The reactions described in schemes 1–2 and the appended Examples may also be carried out using a starting material having an opposite configuration at a carbon center. In this situation, the following two additional steps are required to yield a starting material having an epimeric hydroxyl moiety, i.e. (1) the alcohol is oxidized to its corresponding ketone, (2) the obtained ketone is reduced under selective conditions. Both chiral centers having either (R) or (S) configuration can be obtained selectively and separately.

The compounds, processes and uses of the present invention will be better understood in connection with the following examples, which are intended as an illustration of and not a limitation upon the scope of the invention. Both below and throughout the specification, it is intended that citations to the literature are expressly incorporated by reference.

EXAMPLE 1

(1R,9S,12S,13R,14S,17R,21S,23S,24R,25S,27R)-17-ethyl-1,14-dihydroxy-23,25-dimethoxy-12-{(E)-2-[(1R,3R,4R)-3-methoxy-4-({[(methoxycarbonyl)amino]sulfonyl}oxy)cyclohexyl]-1-methylethenyl}-13,19,21,27-tetramethyl-2,3,10,16-tetraoxo-11,28-dioxa-4-azatricyclo[22.3.1.0$^{4,9}$]octacos-18-ene A solution of chlorosulfonylisocyanate (4.36 ml, 0.05 mol) in benzene (15 mL) was placed into a three necked flask, equipped with a thermometer, a droping funnel and a reflux condenser under a nitrogen atmosphere. The flask was immersed in a water bath. A solution of methanol (2.02 mL, 0.05 mmol) in 3 ml of benzene was added dropwise such that the temperature was maintained in a range of 25–30° C. After complete addition, the mixture was stirred for an additional 30 minutes and allowed to cool to 0–5° C. Hexane (15 mL) was added to the reaction mixture with cooling in an ice bath for 5 minutes. The fine white precepitate was collected by filtration, washed with hexane and dried to afford 8.00 g (92.2%) of the chlorosulfane derivative. A solution of ascomycin (791 mg, 1 methanol (Bundy, G. L. and Peterson. D. C. *Tetrahedron Lett.,* 1978, 41), acetic acid: water (3:1) (Corey, E. J. and Varma. R. K. *J. Am. Chem. Soc.,* 1971, 93, 7319), Dowex 50W-X8 in methanol (Corey, E. I., Ponder, J. W. and Ulrich, P. *Tetrahedron Lett.,* 1980, 21, 137), boron trifluoride etherate in chloroform (Kelly, D. R., Roberts, M. S. and Newton, R. F. *Synth. Commun.* 1979, 9, 295), methanolic hydrogen fluoride (Hanessian, S. and Lavallee, P. *Can. J. Chem.,* 1975, 53, 2975; ibid., 1977, 5, 562), and pyridinuim fluoride in tetrahydrofuran (Nicolaou, K. C.. Seitz, S. P., Pavia, M. R. and Petasis, N. A. *J: Org. Chem.,* 1979, 44. 4011); pyridinium p-toluenesulfonate in ethanol (Prakash, C., Salch, S. and Blair, I. A. *Tetrahedron Lett.,* 1989, 30, 19); N-bromosuccinimide in dimethylsulfoxide (Batten, R. J., Dixon, A. J., Taylor, R. J. K. and Newton, R. F. *Synthesis,* 1980, 234 ); or Tetraethyldiboroxane in the presence of catalytic amounts of trimethylsilyl triflate (Dahlhoff, W. V. and Taba, K. M. *Synthesis,* 1986, 561) and the like.

The reaction temperature is usually conducted from between −40° C. and 60° C., preferably from 0° C. to 50° C. The reaction may require 20 minutes to one day, depending on the reagent chosen.

The reactions described in schemes 1–2 and the appended Examples may also be carried out using a starting material having an opposite configuration at a carbon center. In this situation, the following two additional steps are required to yield a starting material having an epimeric hydroxyl moiety, i.e. (1) the alcohol is oxidized to its corresponding ketone, (2) the obtained ketone is reduced under selective conditions. Both chiral centers having either (R) or (S) configuration can be obtained selectively and separately.

The compounds, processes and uses of the present invention will be better understood in connection with the following examples, which are intended as an illustration of and not a limitation upon the scope of the invention. Both below and throughout the specification, it is intended that citations to the literature are expressly incorporated by reference.

EXAMPLE 1

(1 (R9S,12S,13R,14S,17R,21S,23 S,24R,25S,27R)-7-ethyl-1,14-dihydroxy-23,25-dimethoxy-12-(E)-2-[(1R,3R,4R)-3-methoxy-4-

Analysis calculated for $C_{45}H_{72}N_2O_{16}S$: C, 58.17; H, 7.81; N, 3.01. Found C, 58.88; H, 8.06; N, 2.97.

EXAMPLE 2

(1R,9S12S,13R,14S,17R,21S,23S,24R,25S,27R)-12-{(E)-2-[(1R,3R,4R)-4-({[(ethoxycarbonyl)amino]sulfonyl}oxy)-3-methoxycyclohexyl]-1-methylethenyl}-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting ethanol for methanol.

MS (FAB) m/z: (M+K)$^+$=981;

$^{13}$C NMR (500 MHz in Pyridine-d$_5$) δ211.6 (q), 210.7 (q, minor), 199.5 (q, minor), 198.7 (q), 170.0 (q, minor), 169.9 (q), 167.2 (q), minor), 166.9 (q), 152.3 (q, minor, $_2$NHCOO), 139.3 (q, minor), 138.3 (q), 133.5 (q, minor), 133.1 (q), 131.9 (t), 130.7 (t, minor), 124.5 (t, minor), 124.3 (t), 99.6 (q, minor), 98.8 (q), 86.2 (t, minor), 86.1 (t), 80.8 (t), 80.5 (t), 80.5 (t), 79.5 (t, minor), 77.7 (t, minor), 76.1 (t), 74.7 (t, minor), 74.2 (t), 73.8 (t, minor), 72.9 (t), 69.5 (t), 68.7 (t, minor), 62.4 (s, minor, —NHCOOCH$_2$CH$_3$), 57.6 (p, minor), 57.4 (p), 57.2 (p), 56.9 (t), 56.0 (p), 55.7 (p, minor), 55.4 (t), 55.1 (t, minor), 52.9 (t, minor), 49.2 (s), 48.0 (s, minor), 47.7 (s), 46.4 (s, minor), 44.5 (s, minor), 41.2 (t), 40.8 (t, minor), 39.3 (s), 36.5 (s, minor), 36.4 (s), 35.7 (t), 35.4 (t, minor), 34.5 (s), 34.4 (t, minor), 34.3 (t), 33.0 (s), 32.8 (s, minor), 30.7 (s, minor), 30.7 (s), 30.4 (s, minor), 30.3 (s), 28.1 (s), 27.4 (s, minor), 27.4 (t, minor), 26.7 (t), 25.0 (s, minor), 24.9 (s), 24.7 (s), 24.3 (s, minor), 21.7 (s,. minor), 21.3 (s), 20.4 (p, minor), 19.8 (p), 16.7 (p), 16.7 (p, minor), 16.1 (p, minor), 15.9 (p), 14.3 (p), 13.6 (p, minor), 13.2 (p,), 11.8 (p, minor), 11.7 (p), 10.7 (p), 10.4 (p, minor);

$^1$H NMR (500 MHz in CDCl$_3$) δ0.87 (m, CH$_3$, CH3, major and minor), 0.92 (d, J=5Hz, CH$_3$, minor), 0.95 (d, J=5Hz, CH$_3$), 0.97 (d, J=5Hz, CH$_3$, minor), 1.0 (d, J=5Hz, CH$_3$), 1.06 (m, CH$_2$), 1.1 (m, CH$_2$), 1.33 (t, J=7.5Hz, —NHCOOCH$_2$CH$_3$), 1.41 (s, CH$_3$), 1.43 (s, CH$_3$, minor), 1.45 (s, CH$_3$), 1.48 (s, CH$_3$, minor), 1.56 (m, CH), 1.58 (m, CH$_2$), 1.71 (m, CH$_2$), 2.18 (m, CH$_2$), 2.25 (m, CH), 2.28 (m, CH), 2.35 (m, CH$_2$), 2.70 (ddd, J$_1$=J$_2$=2.5 Hz, J$_3$=17.5Hz, CH, minor), 2.79 (ddd, J$_1$=J$_2$=2.5Hz, J$_3$=15Hz, CH), 3.01 (m, CH$_2$), 3.2 (m, CH), 3.31 (s, OCH$_3$), 3.35 (s, OCH$_3$, minor), 3.39 (s, OCH$_3$, minor), 3.4 (s, OCH$_3$), 3.43 (s, OCH$_3$, minor), 3.43 (s, OCH$_3$), 3.5 (m, CH), 3.6 (m, CH), 3.68 (d, J=10Hz, CH), 3.74 (m, CH, minor), 3.88 (m, CH), 3.92 (m, CH), 3.96 (m, CH, minor), 4.28 (m, OH and —NHCOOCH$_2$CH$_3$), 4.45 (m, CH$_2$), 4.51 (m, CH), 4.63 (d, J=5Hz, CH), 4.83 (s, OH), 5.0–5.05 (m, CH, CH, major and minor), 5.21 (d, J=2.5Hz, CH, minor), 5.33 (d, J=2.5Hz, CH);

Analysis calculated for $C_{46}H_{74}N_2O_{16}S$: C, 58.58; H, 7.90; N, 2.97. Found C, 58.56; H, 8.05; N, 2.91.

EXAMPLE 3

(1R,9S,12S,13R,14S,17R,21 S,23S,24R,25S,27R)-12-((E)-2-{(1R,3R,4R)-4-[({[(benzyloxy)carbonyl]amino]sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting benzyl alcohol for methanol.

MS (FAB) m/z: (M+K)$^+$=1043;

$^{13}$C NMR (500 MHz in Pyridine-d$_5$) δ211.6 (q), 210.7 (q, minor), 199.5 (q, minor), 198.7 (q), 170.0 (q, minor), 169.9 (q), 167.2 (q), minor), 166.9 (q), 152.5 (q, minor, —NHCOO), 139.3 (q, minor), 138.3 (q), 136.4 (q, Ar-C), 133.5 (q, minor), 133.1 (q), 132.0 (t), 130.8 (t, minor), 128.9 (t, Ar—CH), 128.8 (t, Ar—CH), 128.4 (t, Ar—CH), 127.0 (q, Ar-C), 124.5 (t, minor), 124.3 (t), 99.6 (q, minor), 98.8 (q), 86.2 (t, minor), 86.1 (t), 80.8 (t), 80.5 (t), 80.5 (t), 79.5 (t, minor), 77.7 (t, minor), 76.1 (t), 74.7 (t, minor), 74.2 (t), 73.8 (t, minor), 72.9 (t), 69.5 (t), 68.7 (t, minor), 67.9 (s, benylic CH2), 57.6 (p, minor), 57.4 (p), 57.2 (p), 56.9 (t), 56.0 (p), 55.7 (p, minor), 55.4 (t), 55.1 (t, minor), 52.9 (t, minor), 49.2 (s), 48.0 (s, minor), 47.7 (s), 46.4 (s, minor), 44.5 (s, minor), 41.2 (t), 40.8 (t, minor), 39.3 (s), 36.5 (s, minor), 36.4 (s), 35.7 (t), 35.4 (t, minor), 34.5 (s), 34.4 (t, minor), 34.3 (t), 33.0 (s), 32.8 (s, minor), 30.7 (s, minor), 30.7 (s), 30.4 (s, minor), 30.3 (s), 28.1 (s), 27.4 (s, minor), 27.4 (t), 26.7 (t), 25.0 (s, minor), 24.9 (s), 24.7 (s), 24.3 (s, minor), 21.7 (s, minor), 21.3 (s), 20.4 (p, minor), 19.8 (p), 16.7 (p), 16.7 (p, minor), 16.1 (p, minor), 15.9 (p), 13.6 (p, minor), 13.2 (p), 11.8 (p, minor), 11.7 (p), 10.7 (p), 10.4 (p, minor);

$^{1}$H NMR (500 MHz in CDCl$_3$) δ0.87 (m, CH$_3$, CH$_3$, major and minor), 0.92 (d, J=5Hz, CH$_3$, minor), 0.95 (d, J=5Hz, CH$_3$), 0.97 (d, J=5Hz, CH$_3$, minor), 1.0 (d, J=5Hz, CH$_3$), 1.06 (m, CH$_2$), 1.1 (m, CH$_2$), 1.41 (s, CH$_3$), 1.43 (s, CH$_3$, minor), 1.45 (s, CH$_3$), 1.48 (s, CH$_3$, minor), 1.56 (m, CH), 1.58 (m, CH$_2$), 1.71 (m, CH$_2$), 2.18 (m, CH$_2$), 2.25 (m, CH), 2.28 (m, CH), 2.35 (m, CH$_2$), 2.70 (ddd, J$_1$=J$_2$=2.5Hz, J$_3$=17.5Hz, CH, minor), 2.79 (ddd, J$_1$=J$_2$=2.5Hz, J$_3$=15Hz, CH), 3.01 (m, CH$_2$), 3.2 (m, CH), 3.31 (s, OCH$_3$), 3.35 (s, OCH$_3$, minor), 3.39 (s, OCH$_3$, minor), 3.4 (s, OCH$_3$), 3.43 (s, OCH$_3$), 3.43 (s, OCH$_3$), 3.5 (m, CH), 3.6 (m, CH), 3.68 (d, J=10Hz, CH), 3.74 (m, CH, minor), 3.88 (m, CH), 3.92 (m, CH), 3.96 (m, CH, minor), 4.28 (s, OH), 4.45 (m, CH$_2$), 4.51 (m, CH), 4.63 (d, J=5Hz, CH), 4.86 (s, OH), 5.0–5.05 (m, CH, CH, major and minor), 5.21 (d, J=2.5Hz, CH, minor), 5.33 (d, J=2.5Hz, CH), 7.4 (m, 4H, ArCH);

Analysis calculated for C$_{51}$H$_{76}$N$_2$O$_{16}$S: C, 60.93; H, 7.62; N, 2.78. Found C, 60.65; H, 7.78; N, 2.71.

EXAMPLE 4

(1R,9S,12S,13R,14S,17R,21S,23S,24R,25S,27R)-12-{(E)-2-[(1R,3R,4R)-4-({[(tert-butoxycarbonyl)amino]sulfonyl}oxy)-3-methoxycyclohexyl]-1-methylethenyl}-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting tert-butyl alcohol for methanol.

MS (FAB) m/z: (M+K)$^{+}$=1009;

$^{13}$C NMR (500 MHz in Pyridine-d$_5$) δ211.6 (q), 210.8 (q, minor), 199.6 (q, minor), 198.8 (9-CO), 170.1 (q, minor), 170.0 (q), 167.3 (q, minor), 167.0 (q), 151.1 (q, minor, —NHCOO), 139.4 (q, minor), 138.4 (q), 133.6 (q, minor), 133.2 (q), 132.0 (t), 130.9 (t, minor), 124.6 (t, minor), 124.5 (t), 99.7 (q, minor), 98.9 (q), 86.5 (t, minor), 86.4 (t), 82.4 (q), 80.9 (t, minor), 80.8 (t), 80.7 (t), 79.6 (t, minor), 77.9 (t, minor), 76.3 (t), 74.8 (t, minor), 74.3 (t), 74.0 (t, minor), 73.1 (t), 69.7 (t), 68.8 (t, minor), 57.7 (p, minor), 57.6 (p), 57.0 (t), 56.2 (p), 55.9 (p, minor), 55.6 (t), 55.3 (t, minor), 53:0 (t, minor), 49.4 (s), 48.0 (s, minor), 47.9 (s), 46.5 (s, minor), 44.6 (s, minor), 41.4 (t), 41.0 (t, minor), 39.4 (s), 36.9 (s, minor), 36.7 (s), 35.9 (t), 35.5 (t, minor), 35.1 (s, minor), 34.5 (t), 34.5 (s), 33.1 (s), 32.9 (s, minor), 31.9 (t), 30.8 (s, minor), 30.7 (s), 30.6 (s, minor), 30.5 (s), 28.2 (s), 28.1 (pt-butyl group), 27.6 (t, minor), 27.5 (s, minor), 26.6 (t), 25.2 (s, minor), 25.0 (s), 24.8 (s), 24.4 (s, minor), 21.8 (s, minor), 21.5 (s), 20.6 (p, minor), 20.0 (p), 16.9 (p), 16.8 (p, minor), 16.3 (p, minor), 16.0 (p), 13.7 (p, minor), 13.3 (p), 12.0 (p, minor), 11.9 (p), 10.8 (p), 10.5 (p, minor);

$^{1}$H NMR (500 MHz in Pyridine-d$_5$) δ0.82 (t, J=7.5Hz, CH$_3$), 0.86 (t, J=7.5Hz, CH$_3$, minor), 0.94 (s, CH$_3$), 0.96 (s, CH$_3$, minor), 1.15 (d, J=7.5Hz, CH$_3$, minor), 1.19 (d, J=7.5Hz, CH$_3$), 1.26 (d, J=7.5Hz, CH$_3$), 1.54 (s, t-butyl group), 1.62 (s, CH$_3$), 1.78 (s, CH$_3$), 2.4 (s, CH$_3$, minor), 2.21 (m, CH$_2$), 2.29 (m, CH$_2$), 2.43 (m, CH$_2$ and CH), 2.57 (m, CH), 2.66 (ddd, J1=J2=7.5Hz, J3=15Hz, CH$_2$), 2.76 (m, CH, minor), 2.9 (ddd, J1=J2=7.5Hz, J3=15Hz, CH$_2$, minor), 3.01 (m, CH$_2$, minor), 3.07 (ddd, J1=J2=7.5Hz, J3=15Hz, CH$_2$), 3.22 (m, CH$_2$), 3.41 (s, OCH$_3$, minor), 3.415 (s, OCH$_3$), 3.42 (s, OCH$_3$), 3.43 (s, OCH$_3$), 3.53 (m, CH), 3.67 (m, CH), 3.87 (CH, major and minor), 4.19 (d, J=10Hz, CH), 4.27 (ddd, J1=J2=2.5Hz, J3=10Hz, CH, minor), 4.46 (m, CH), 4.56 (m, CH, minor), 4.69 (br.b, J=15Hz, CH$_2$), 4.88 (m, CH), 5.09 (m, CH), 5.11 (m, CH), 5.13 (m, CH, minor), 5.35 (m, CH, minor), 5.38 (m, CH), 5.52 (m, CH, minor), 5.78 (d, J=5Hz, CH), 5.84 (d, J=5Hz, CH, minor);

Analysis calculated for C$_{48}$H$_{78}$N$_2$O$_{16}$S: C, 59.36; H,8.09; N, 2.88. Found C, 59.16; H, 8.16; N, 2.72.

EXAMPLE 5

(1R,9S,12S,13R,14S,17R,21S,23S,24R,25S,27R)-12-((E)-2-{(1R,3R.4R)-4-[({[(cyclopentyloxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting cyclopentyl alcohol for methanol.

MS (FAB) m/z: (M+K)$^{+}$=982;

$^{13}$C NMR (500 MHz in Pyridine-d$_5$) δ211.6 (q), 210.8 (q, minor), 199.6 (q, minor), 198.8 (q), 170.1 (q, minor), 170.0 (q), 167.3 (q, minor), 167.0 (q), 152.1 (q, minor, —NHCOO—), 139.4 (q, minor), 138.4 (q), 133.6 (q, minor), 133.2 (q), 132.0 (t), 130.8 (t, minor), 124.6 (t, minor), 124.5 (t), 99.7 (q, minor), 98.9 (q), 86.3 (t, minor), 86.3 (t), 80.8 (t, minor), 80.7 (t), 80.7 (t), 79.6 (t, minor), 77.9 (t, minor), 76.3 (t), 74.8 (t, minor), 74.3 (t), 74.0 (t, minor), 73.1 (t), 69.7 (t), 68.8 (t, minor), 57.7 (p, minor), 57.5 (p), 57.5 (p), 57.0 (t), 56.2 (p), 55.9 (p, minor), 55.6 (t), 55.3 (t, minor), 53.0 (t, minor), 49.4 (s), 48.0 (s, minor), 47.9 (s), 46.5 (s, minor), 44.6 (s, minor), 41.4 (t), 41.0 (t, minor), 39.4 (s), 36.7 (s, minor), 36.7 (s), 35.9 (t), 35.5 (t, minor), 35.1 (s, minor), 34.5 (t), 33.1 (s), 33.0 and 32.9 (s, minor, pentyl ring), 30.9 (s, minor), 30.9 (s), 30.6 (s, minor), 30.5 (s), 28.2 (s), 27.6 (t, minor), 27.5 (s, minor), 26.6 (t), 25.2 (s, minor), 25.0 (s), 24.8 (s), 24.4 (s, minor), 23.9 and 23.8 (s, minor, pentyl ring), 21.8 (s, minor), 21.5 (s), 20.6 (p, minor), 20.0 (p), 16.9 (p), 16.8 (p, minor), 16.3 (p, minor), 16.0 (p), 13.7 (p, minor), 13.3 (p), 12.0 (p, minor), 11.9 (p), 10.8 (p), 10.5 (p, minor);

$^{1}$H NMR (500 MHz in Pyridine-d$_5$) δ0.82 (t, J=7.5Hz, CH$_3$), 0.86 (t, J=7.5Hz, CH$_3$, minor), 0.94 (s, CH$_3$), 0.96 (s, CH$_3$, minor), 1.15 (d, J=7.5Hz, CH$_3$, minor), 1.19 (d, J=7.5Hz, CH$_3$), 1.26 (d, J=7.5Hz, CH$_3$), 1.45 (m, cyclopentyl CH$_2$), 1.62 (s, CH$_3$), 1.78 (s, CH$_3$), 1.84 (s, CH$_3$, minor), 2.21 (m, CH$_2$), 2.29 (m, CH$_2$), 2.43 (m, CH$_2$ and CH), 2.57 (m, CH), 2.66 (ddd, J$_1$=J$_2$=7.5Hz, J$_3$=15Hz, CH$_2$), 2.76 (m, CH, minor), 2.9 (ddd, J$_1$=J$_2$=7.5Hz, J$_3$=15Hz, CH$_2$, minor), 3.01 (m, CH$_2$, minor), 3.07 (ddd, J$_1$=J$_2$=7.5Hz, J$_3$=15Hz, CH$_2$), 3.22 (m, CH$_2$), 3.41 (s, OCH$_3$, minor), 3.415 (s, OCH$_3$), 3.42 (s, OCH$_3$), 3.43 (s, OCH$_3$), 3.53 (m, CH), 3.67 (m, CH), 3.87 (CH, major and minor), 4.19 (d, J=10Hz, CH), 4.27 (ddd, J$_1$=J$_2$=2.5Hz, J$_3$=10Hz, CH, minor), 4.46 (m, m, CH), 4.56 (m, CH, minor), 4.69 (br.b, J=15Hz, CH$_2$), 4.84 (m, CH), 5.08 (m, CH), 5.11 (m, CH), 5.13 (m, CH, minor), 5.33 (m, CH, minor), 5.35 (m, CH). 5.56 (m, CH, minor), 5.77 (d, J=5Hz, CH), 5.83 (d, J=5Hz, CH, minor);

Analysis calculated for C$_{49}$H$_{78}$N$_2$O$_{16}$S: C, 59.85; H, 7.99; N, 2.84. Found C, 59.53; H, 8.19; N, 2.53.

EXAMPLE 6

(1R,9S,12S,13R,14S,17R,21S,23S,24R,25S,27R)-12-((E)-2-{(1R,3R,4R)-4-[({[(cyclohexyloxy) carbonyl]amino}sulfonyl)oxy]-3-methoxycyclohexyl}-1-methylethenyl)-17-ethyl-1, 14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting cyclohexyl alcohol for methanol.

MS (FAB) m/z: (M+K)$^+$=1073;

$^{13}$C NMR (500 MHz in Pyridine-d$_5$) δ211.6 (q), 210.8 (q, minor), 199.6 (q, minor), 198.8 (q), 170.1 (q, minor), 170.0 (q), 167.3 (q), minor), 167.0 (q), 151.9 (q, minor, —NHCOO), 139.4 (q, minor), 138.4 (q), 133.6 (q, minor), 133.3 (q), 132.0 (t), 130.8 (t, minor), 124.6 (t, minor), 124.5 (t), 99.7 (q, minor), 98.9 (q), 86.4 (t, minor), 86.3 (t), 80.7 (t), 80.7 (t), 79.5 (t, minor), 77.9 (t, minor), 76.3 (t), 75.0 (t, minor, hexyl ring), 74.8 (t, minor), 74.3 (t), 74.0 (t, minor), 73.1 (t), 69.7 (t), 68.9 (t, minor), 57.7 (p, minor), 57.5 (p), 57.5 (p), 57.0 (t), 56.2 (p), 55.9 (p, minor), 55.5 (t), 55.3 (t, minor), 53.0 (t, minor), 49.4 (s), 48.0 (s, minor), 47.9 (s), 46.5 (s, minor), 44.6 (s, minor), 41.4 (t), 41.0 (t, minor), 39.4 (s), 36.7 (s, minor), 36.7 (s), 35.9 (t), 35.5 (t, minor), 34.5 (t, minor), 34.4 (t), 33.1 (s), 32.9 (s, minor), 31.9 (s, minor, hexyl ring), 30.9 (s, minor), 30.8 (s), 30.6 (s, minor), 30.5 (s), 28.2 (s), 27.5 (s, minor), 27.5 (t, minor), 26.6 (t), 25.5 (s, minor, hexyl ring), 25.2 (s, minor), 25.0 (s), 24.8 (s), 24.4 (s, minor), 23.8, 23.7 (s, minor, hexyl ring, 2x CH$_2$), 21.8 (s, minor), 21.5 (s), 20.6 (p), 20.0 (p), 16.9 (p), 16.8 (p, minor), 16.3 (p, minor), 16.0 (p), 13.7 (p, minor), 13.3 (p), 12.0 (p, minor), 11.9 (p), 10.8 (p), 10.5 (p, minor).

$^1$H NMR (500 MHz in Pyridine-d$_5$) δ0.82 (t, J=7.5Hz, CH$_3$), 0.86 (t, J=7.5Hz, CH$_3$, minor), 0.93 (s, CH$_3$), 0.95 (s, CH$_3$, minor), 1.14, 1.18 (m, CH$_3$ minor and CH$_3$, minor), 1.18 (d, J=7.5 Hz, CH$_3$), 1.26 (d, J=7.5Hz, CH$_3$), 1.35 (m, cyclohexylCH$_2$), 1.51 (m, cyclohexylCH$_2$), 1.62 (s, CH$_3$), 1.77 (s, CH$_3$), 1.83 (s, CH$_3$, minor), 1.91 (m, cyclohexylCH$_2$), 2.2 (m, CH$_2$), 2.28 (m, CH$_2$), 2.43 (m, CH$_2$, CH), 2.57 (m, CH), 2.66 (ddd, J$_1$=J$_2$=7.5Hz, J$_3$=15Hz, CH), 2.76 (m, CH, minor), 2.89 (ddd, J$_1$=J$_2$=7.5Hz, J$_3$=15Hz, CH, minor), 3.01 (m, CH, minor), 3.06 (ddd, J$_1$=J$_2$=7.5Hz, J$_3$=15Hz, CH), 3.21 (m, CH$_2$), 3.40, 3.42, 3.43 (s, OCH$_3$, OCH$_3$ and OCH$_3$), 3.53 (m, CH), 3.66 (m, CH), 3.88 (m, CH), 3.89 (m, CH, minor),, 4.18 (d, J=10Hz, CH), 4.27 (dd, J$_1$=5Hz, J$_2$=10Hz, CH, minor), 4.47 (m, CH), 4.55 (m, CH, minor), 4.69 (br.d, J=OHz, CH$_2$), 4.86 (m, CH), 4.95 (m, cyclohexyl ring, CH), 5.09 (m, CH), 5.11 (m, CH and CH, minor), 5.33 (m, CH, minor), 5.36 (m, CH), 5.51 (d, J=5Hz, CH), 5.77 (d, J=5Hz, CH), 5.83 (d, J=5Hz, CH, minor);

Analysis calculated for C$_{50}$H$_{80}$N$_2$O$_{16}$S: C, 60.22; H, 8.08; N, 2.80. Found C, 59.93; H, 7.92; N, 2.60.

EXAMPLE 7

(1R,9S,12S,13R,14S,17R,21S,23S,24R,25S,27R)-12-((E)-2-{(1R,3R,4R)-4-[({[(cycloheptyloxy) carbonyl]amino}sulfonyl)oxy]-3-methoxycyclohexyl}-1-methylethenyl)-17-ethyl-1, 14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting cycloheptyl alcohol for methanol.

MS (FAB) m/z: (M+K)$^+$=1049;

$^{13}$C NMR (500 MHz in Pyridine-d$_5$) δ211.5 (q), 210.7 (q, minor), 199.6 (q, minor), 198.8 (q), 170.1 (q, minor), 170.0 (q), 167.3 (q, minor), 167.0 (q), 151.8 (q, minor, —NHCOO), 139.4 (q, minor), 138.4 (q), 133.6 (q, minor), 133.3 (q), 132.0 (t), 130.8 (t, minor), 124.6 (t, minor), 124.5 (t), 99.7 (q, minor), 98.9 (q), 86.3 (t), 80.7 (t), 79.5 (26—CH, minor), 77.9 (t, minor), 77.6 (t, minor, heptyl ring), 76.3 (t), 74.8 (t, minor), 74.3 (t), 74.0 (t, minor), 73.1 (t), 69.6 (t), 68.8 (t, minor), 57.7 (p, minor), 57.5 (p), 57.5 (p), 57.0 (t), 56.1 (p), 55.8 (p, minor), 55.5 (t), 55.3 (t), minor), 53.0 (t, minor), 49.3 (s), 48.0 (s), 47.9 (s, minor), 46.5 (s, minor), 44.6 (s, minor), 41.4 (t), 41.0 (t, minor), 39.4 (s), 36.7 (s), 35.9 (t), 35.5 (t, minor), 35.1 (s, minor), 34.4 (t), 34.1 (s, minor, heptyl ring), 33.1 (s), 32.9 (s, minor), 30.8 (s), 30.5 (s), 28.4 (s, minor, heptyl ring), 28.2 (s, minor), 27.5 (t, minor), 26.6 (t), 25.2 (s, minor), 25.0 (s), 24.8 (s), 24.4 (s, minor), 22.9 (s, minor, heptyl ring), 21.8 (s, minor), 21.5 (s), 20.6 (p, minor), 20.0 (p), 16.9 (p), 16.8 (p, minor), 16.3 (p), 16.0 (p), 13.7 (p, minor), 13.3 (p), 12.0 (p, minor), 11.8 (p), 10.7 (p), 10.5 (p, minor);

$^1$H NMR (500 MHz in Pyridine-d$_5$) δ0.82 (t, J=7.5Hz, CH$_3$), 0.86 (t, J=7.5Hz, CH$_3$, minor), 0.93 (s, CH$_3$), 0.95 (s, CH$_3$, minor), 1.14, 1.18 (m, CH$_3$ and CH$_3$, minor), 1.18 (d, J=7.5 Hz, CH$_3$), 1.26 (d, J=7.5Hz, CH$_3$), 1.4 (m, cycloheptyl ring, CH$_2$), 1.56 (m, cycloheptyl ring, CH$_2$), 1.62 (s, CH$_3$), 1.77 (s, CH$_3$), 1.83 (s, CH$_3$, minor), 1.97 (m, cycloheptyl ring, CH$_2$), 2.2 (m, CH$_2$), 2.28 (m, CH$_2$), 2.43 (m, CH$_2$, CH), 2.57 (m, CH), 2.66 (ddd, J$_1$=J$_2$=7.5Hz, J$_3$=15Hz, CH), 2.76 (m, CH, minor), 2.89 (ddd, J$_1$=J$_2$=7.5Hz, J$_3$=15Hz, CH, minor), 3.01 (m, CH, minor), 3.06 (ddd, J$_1$=J$_2$=7.5Hz, J$_3$=15Hz, CH), 3.21 (m, CH$_2$), 3.40, 3.42, 3.43 (s, OCH$_3$, OCH$_3$ and OCH$_3$), 3.53 (m, CH), 3.66 (m, CH), 3.88 (m, CH), 3.89 (m, CH, minor), 4.18 (d, J=10Hz, CH), 4.27 (dd, J$_1$=5Hz, J$_2$=10Hz, CH, minor), 4.47 (m, CH), 4.55 (m, CH, minor), 4.69 (br.d, J=10Hz, CH$_2$), 4.86 (m, CH), 5.09 (m, CH), 5.11 (m, CH and CH, minor), 5.33 (m, CH, minor), 5.36 (m, CH), 5.51 (d, J=5Hz, CH), 5.77 (d, J=5Hz, CH), 5.83 (d, J=5Hz, CH, minor);

Analysis calculated for C$_{51}$H$_{82}$N$_2$O$_{16}$S: C, 60.57; H, 8.17; N, 2.77. Found C, 60.21; H, 8.08; N, 2.68.

EXAMPLE 8

(1R,9S,12S,13R,14S,17R,21S,23S,24R,25S,27R)-17-ethyl-1,14-dihydroxy-23,25-dimethoxy-12-((E)-2-{(1R,3R,4R)-3-methoxy-4-[({[(4-pyridinylmethoxy)carbonyl]amino}sulfonyl)oxy] cycyclohexyl}-1-methylethenyl)-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting 4-pyridyl methyl alcohol for methanol.

MS (FAB) n/z: (M+2K-H)$^+$=1082;

$^{13}$C NMR (500 MHz in Pyridine-d$_5$) δ211.7 (q), 210.9 (q, minor), 199.7 (cl, minor), 199.0 (q), 170.2 (q, minor), 170.1 (q), 167.4 (q, minor), 167.1 (q), 162.4 and 162.1 (q, CF$_3$COO), 152.7 (q, minor, —NHCOO—), 145.6 (q, Ar-C), 139.5 (q, minor), 138.5 (q), 133.8 (q, minor), 133.4 (q), 132.1 (t), 130.9 (t, minor), 124.7 (t, minor), 124.5 (t), 122.3 (t, Ar—CH), 99.8 (q, minor), 99.0 (q), 86.3 (t, minor), 86.3 (t), 80.8 (t, minor), 80.7 (t), 80.7 (t), 77.9 (t, minor), 76.3 (t), 74.8 (t, minor), 74.3 (t), 74.0 (t, minor), 73.1 (t), 69.7 (t), 68.8 (t, minor), 66.1 (s, pyridyl—CH$_2$), 57.7 (p, minor), 57.5 (p), 57.5 (p), 57.0 (t), 56.2 (p), 55.9 (p, minor), 55.6 (t), 55.3 (t, minor), 53.0 (t, minor), 49.4 (s), 48.0 (s, minor), 47.9 (s), 46.5 (s, minor), 44.6 (s, minor), 41.4 (t), 41.0 (t, minor), 39.4 (s), 37.0 (s, minor), 36.6 (s), 35.9 (t), 35.5 (t, minor), 35.1 (s, minor), 34.5 (t), 33.1 (s), 30.9 (s, minor), 30.9 (s), 30.6 (s, minor), 30.5 (s), 28.2 (s), 27.6 (t, minor), 27.5 (s, minor), 26.6 (t), 25.2 (s, minor), 25.0 (s), 24.8 (s), 24.4 (s, minor), 21.8 (s, minor), 21.5 (s), 20.6 (p, minor), 20.0 (p), 16.9 (p), 16.8 (p, minor), 16.3 (p, minor), 16.0 (p), 13.7 (p, minor), 13.3 (p), 12.0 (p, minor), 11.9 (p), 10.8 (p), 10.5 (p, minor);

$^1$H NMR (500 MHz in Pyridine-d$_5$) δ0.82 (t, J=7.5Hz, CH$_3$), 0.86 (t, J=7.5Hz, CH$_3$, minor), 0.94 (s, CH$_3$), 0.96 (s, CH$_3$, minor), 1.15 (d, J=7.5Hz, CH$_3$, minor), 1.19 (d, J=7.5Hz, CH$_3$), 1.26 (d, J=7.5Hz, CH$_3$), 1.62 (s, CH$_3$), 1.78 (s, CH$_3$), 1.84 (s, CH$_3$, minor), 2.21 (m, CH$_2$), 2.29 (m, CH$_2$), 2.43 (m, CH$_2$ and CH), 2.57 (m, CH), 2.66 (ddd, J$_1$=J$_2$=7.5Hz, J$_{3=15}$Hz, CH$_2$), 2.76 (m, CH, minor), 2.9 (m, CH$_2$, minor), 3.01 (m, CH$_2$, minor), 3.07 (m, CH$_2$), 3.22 (m, CH$_2$), 3.36 (s, OCH$_3$), 3.4 (s, OCH$_3$), 3.42 (s, OCH$_3$), 3.43 (s, OCH$_3$, minor), 3.53 (m, CH), 3.67 (m, CH), 3.87 (CH, major and minor), 4.19 (d, J=10Hz, CH), 4.27 (ddd, J$_1$=J$_2$=2.5Hz, J$_3$=10Hz, CH, minor), 4.46 (m, m, CH), 4.56 (m, CH, minor), 4.69 (m, CH$_2$), 4.82 (m, CH), 5.08 (m, CH), 5.11 (m, CH), 5.13 (m, CH, minor), 5.33 (m, CH, minor), 5.35 (m, CH), 5.44 (s, pyridyl—CH$_2$), 5.56 (in, CH, minor), 5.77 (m, CH), 5.83 (m, CH, minor), 7.41 (d, 2H, J=5Hz, Ar-H), 7.51 (d, 2H, J=5Hz, Ar-H).

EXAMPLE 9

(1R,9S,12S,13R,14S,17R,21S,23S,24R,25S,27R)-17-ethyl-1,14-dihydroxy-23,25-dimethoxy-12-((E)-2-{(1R,3R,4R)-3-methoxy-4-[({[(3-pyridinylmethoxy)carbonyl]amino}sulfonyl)oxy]cyclohexyl}-1-methylethenyl)-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting 3-pyridyl methyl alcohol for methanol.

MS (FAB) m/z: (M+K)$^+$=1044, (M+2K-H)$^+$=1082

$^{13}$C NMR (500 MHz in Pyridine-d$_5$) δ211.6 (q), 210.8 (q, minor), 199.7 (q, minor), 198.9 (q), 170.1 (q, minor), 170.0 (q), 167.3 (q, minor), 167.0 (q), 162.4 and 162.1 (q, CF$_3$COO), 152.6 (q, minor, —NHCOO—), 139.4 (q, minor), 138.4 (q), 136.2 (t, Ar—CH), 133.7 (q, minor), 133.3 (q), 132.1 (t), 130.8 (t, minor), 124.6 (t, minor), 124.5 (t), 99.7 (q, minor), 98.9 (q), 86.3 (t, minor), 86.3 (t), 80.8 (t, minor), 80.7 (t), 80.7 (t), 77.9 (t, minor), 76.3 (t), 74.8 (t, minor), 74.3 (t), 74.0 (t, minor), 73.1 (t), 69.7 (t), 68.8 (t, minor), 65.7 (s, pyridyl-CH2), 57.7 (p, minor), 57.5 (p), 57.5 (p), 57.0 (t), 56.2 (p), 55.9 (p, minor), 55.6 (t), 55.3 (t, minor), 53.0 (t, minor), 49.4 (s), 48.0 (s, minor), 47.9 (s), 46.5 (s, minor), 44.6 (s, minor), 41.4 (t), 41.0 (t, minor), 39.4 (s), 36.9 (s, minor), 36.5 (s), 35.9 (t), 35.5 (t, minor), 35.1 (s, minor), 34.5 (t), 33.1 (s), 30.9 (s, minor), 30.9 (s), 30.6 (s, minor), 30.5 (s), 28.2 (s), 27.6 (t, minor), 27.5 (s, minor), 26.6 (t), 25.2 (s, minor), 25.0 (s), 24.8 (s), 24.4 (s, minor), 21.8 (s, minor), 21.5 (s), 20.6 (p, minor), 20.0 (p), 16.9 (p), 16.8 (p, minor), 16.3 (p, minor), 16.0 (p), 13.7 (p, minor), 13.3 (p), 12.0 (p, minor), 11.9 (p), 10.8 (p), 10.5 (p, minor);

$^1$H NMR (500 MHz in Pyridine-d$_5$) δ0.82 (t, J=7.5Hz, CH$_3$), 0.86 (t, J=7.5Hz, CH$_3$, minor), 0.94 (s, CH$_3$), 0.96 (s, CH$_3$, minor), 1.15 (d, J=7.5Hz, CH$_3$, minor), 1.19 (d, J=7.5Hz, CH$_3$), 1.26 (d, J=7.5Hz, CH$_3$), 1.62 (s, CH$_3$), 1.78 (s, CH$_3$), 1.84 (s, CH$_3$, minor), 2.21 (m, CH$_2$), 2.29 (m, CH$_2$), 2.43 (m, CH$_2$ and CH), 2.57 (m, CH), 2.66 (ddd, J$_{12}$=7.5Hz, J$_3$=15Hz, CH$_2$), 2.76 (m, CH, minor), 2.9 (ddd, J$_1$=J$_2$=7.5Hz, J$_3$=15Hz, CH$_2$, minor), 3.01 (m, CH$_2$, minor), 3.07 (m, CH$_2$), 3.22 (m, CH$_2$), 3.36 (s, OCH$_3$), 3.4 (s, OCH$_3$), 3.42 (s, OCH$_3$), 3.43 (s, OCH$_3$, minor), 3.53 (m, CH), 3.67 (m, CH), 3.87 (m, CH, major and minor), 4.19 (d, J=10Hz, CH), 4.27 (ddd, J$_1$=J$_2$=2.5Hz, J$_3$=10Hz, CH, minor), 4.46 (m, CH), 4.56 (m, CH, minor), 4.69 (m, CH$_2$), 4.8 (m, CH), 4.91 (s, CH), 5.08 (m, CH), 5.11 (m, CH), 5.13 (m, CH, minor), 5.33 (m, CH, minor), 5.35 (m, CH), 5.43 (s, pyridyl—CH$_2$), 5.56 (d, J=5Hz, CH, minor), 5.77 (d, J=5Hz, CH), 5.83 (d, J=5Hz, CH, minor), 7.25 (m, ArCH), 7.81 (m, ArCH), 8.68 (m, ArCH), 8.90 (m, ArCH).

EXAMPLE 10

(1R,9S,12S.13R,14S,17R,21S,23S,24R,25S,27R)-17-ethyl-1,14-dihydroxy-23,25-dimethoxy-12-((E)-2-[(1R,3R,4R)-3-methoxy-4-[({[(2-pyridinylmethoxy)carbonyl]amino}sulfonyl)oxy]cyclohexyl]-1-methylethenyl)-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting 2-pyridyl methyl alcohol for methanol.

MS (FAB) m/z: (M+K)$^+$=1044, (M+2K-H)$^+$=1082;

$^{13}$C NMR (500 MHz in Pyridine-d$_5$) δ211.6 (q), 210.8 (q, minor), 199.7 (q, minor), 198.9 (q), 170.1 (q, minor), 170.0 (q), 167.3 (q, minor), 167.0 (q), 162.4 and 162.1 (q, CF$_3$COO), 156.4 (q, Ar-C), 152.6 (q, minor, —NHCOO), 139.4 (q, minor), 138.4 (q), 137.1 (t, Ar—CH), 136.8 (t, Ar—CH), 133.7 (q, minor), 133.3 (q), 132.1 (t), 130.8 (t, minor), 124.6 (t, minor), 124.5 (t), 122.0 (t, Ar—CH), 99.7 (q, minor), 98.9 (q), 86.3 (t, minor), 86.3 (t), 80.8 (t, minor), 80.7 (t), 80.7 (t), 77.9 (t, minor), 76.3 (t), 74.8 (t, minor), 74.3 (t), 74.0 (t, minor), 73.1 (t), 69.7 (t), 68.8 (t, minor), 68.6 (s, pyridyl—CH$_2$), 57.7 (p, minor), 57.5 (p), 57.5 (p), 57.0 (t), 56.2 (p), 55.9 (p, minor), 55.6 (t), 55.3 (t, minor), 53.0 (t, minor), 49.4 (s), 48.0 (s, minor), 47.9 (s), 46.5 (s,.minor), 44.6 (s, minor), 41.4 (t), 41.0 (t, minor), 39.4 (s), 36.9 (s, minor), 36.5 (s), 35.9 (t), 35.5 (t, minor), 35.1 (s, minor), 34.5 (t), 33.1 (s), 30.9 (s, minor), 30.9 (s), 30.6 (s, minor), 30.5 (s), 28.2 (s), 27.6 (t, minor), 27.5 (s, minor), 26.6 (t), 25.2 (s, minor), 25.0 (s), 24.8 (s), 24.4 (s, minor), 21.8 (s, minor), 21.5 (s), 20.6 (p, minor), 20.0 (p), 16.9 (p), 16.8 (p, minor), 16.3 (p, minor), 16.0 (p), 13.7 (p, minor), 13.3 (p), 12.0 (p, minor), 11.9 (p), 10.8 (p), 10.5 (p, minor);

$^1$H NMR (500 MHz in Pyridine-d$_5$) δ0.82 (t, J=7.5Hz, CH$_3$), 0.86 (t, J=7.5Hz, CH$_3$, minor), 0.94 (s, CH$_3$), 0.96 (s, CH$_3$, minor), 1.15 (d, J=7.5Hz, CH$_3$, minor), 1.19 (d, J=7.5Hz, CH$_3$), 1.26 (d, J=7.5Hz, CH$_3$), 1.62 (s, CH$_3$), 1.78 (s, CH$_3$), 1.84 (s, CH$_3$, minor), 2.21 (m, CH$_2$), 2.29 (m, CH$_2$), 2.43 (m, CH$_2$ and CH), 2.57 (m, CH), 2.66 (ddd, J$_1$=J$_2$=7.5HZ, J$_3$=15Hz, CH$_2$), 2.76 (m, CH, minor), 2.9

(ddd, $J_1=J_2=7.5Hz$, $J_3=15Hz$, $CH_2$, minor), 3.01 (m, $CH_2$, minor), 3.07 (m, $CH_2$), 3.22 (m, $CH_2$), 3.36 (s, $OCH_3$), 3.4 (s, $OCH_3$), 3.42 (s, $OCH_3$), 3.43 (s, $OCH_3$, minor), 3.53 (m, CH), 3.67 (m, CH), 3.87 (CH, major and minor), 4.19 (d, J=10Hz, CH), 4.27 (ddd, $J_1=J_2=2.5Hz$, $J_3=10Hz$, CH, minor), 4.46 (m, CH), 4.56 (m, CH, minor), 4.69 (m, $CH_2$), 4.82 (m, CH), 5.08 (m, CH), 5.11 (m, CH), 5.13 (m, CH, minor), 5.33 (m, CH, minor), 5.35 (m, CH), 5.56 (m, CH, minor), 5.60 (d, J=5Hz, pyridyl—$CH_2$), 5.77 (m, CH), 5.83 (m, CH, minor), 7.12 (t, J=7.5Hz, ArCH), 7.17 (t, J=7.5Hz, ArCH), 7.53 (d, J=7.5Hz, ArCH), 7.63 (m, ArCH), 7.77 (d, J=7.5Hz, ArCH).

EXAMPLE 11

(1R,9S,12S,13R,14S,17R,21S,23S,24R,25S,27R)-17-ethyl-1,14-dihydroxy-23,25-dimethoxy-12-[(E)-2-((1R,3R,4R)-3-methoxy-4-{[({[(4-nitrobenzyl)oxy]carbonyl}amino)sulfonyl]oxy}cyclohexyl)-1-methylethenyl]-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting 4-nitrobenzyl alcohol for methanol.

MS (FAB) m/z: (M+K)$^+$=1088, (M+2K-H)$^+$=1126;

$^{13}$C NMR (500 MHz in Pyridine-d$_5$) δ211.5 (q), 210.7 (q, minor), 199.7 (q, minor), 198.9 (q), 170.1 (q, minor), 170.0 (q), 167.3 (q, minor), 167.0 (q), 152.5 (q, minor, —NHCOO—), 148.0 (q, Ar-C-NO2), 144.0 (q, Ar-C—CH$_2$O), 139.4 (q, minor), 138.4 (q), 137.1 (t, Ar-CH), 136.8 (t, Ar—CH), 133.7 (q, minor), 133.3 (q), 132.1 (t), 130.8 (t, minor), 128.6 (t, Ar-CH), 124.6 (t, minor), 124.5 (t), 124.0 (t, Ar—CH), 99.7 (q, minor), 98.9 (q), 86.3 (t, minor), 86.3 (t), 80.8 (t, minor), 80.7 (t), 80.7 (t), 77.9 (t, minor), 76.3 (t), 74.8 (t, minor), 74.3 (t), 74.0 (t, minor), 73.1 (t), 69.7 (t), 68.8 (t, minor), 66.5 (s, benzyl—$CH_2$), 57.7 (p, minor), 57.5 (p), 57.5 (p), 57.0 (t), 56.2 (p), 55.9 (p, minor), 55.6 (t), 55.3 (t, minor), 53.0 (t, minor), 49.4 (s), 48.0 (s, minor), 47.9 (s), 46.5 (s, minor), 44.6 (s, minor), 41.4 (t), 41.0 (t, minor), 39.4 (s), 36.9 (s, minor), 36.5 (s), 35.9 (t), 35.5 (t, minor), 35.1 (s, minor), 34.5 (t), 33.1 (s), 30.9 (s, minor), 30.9 (s), 30.6 (s, minor), 30.5 (s), 28.2 (s), 27.6 (t, minor), 27.5 (s, minor), 26.6 (t), 25.2 (s, minor), 25.0 (s), 24.8 (s), 24.4 (s, minor), 21.8 (s), 21.5 (s), 20.6 (p, minor), 20.0 (p), 16.9 (p), 16.8 (p, minor), 16.3 (p, minor), 16.0 (p), 13.7 (p, minor), 13.3 (p), 12.0 (p, minor), 11.9 (p), 10.8 (p), 10.5 (p, minor);

$^1$H NMR (500 MHz in Pyridine-d$_5$) δ0.82 (t, J=7.5Hz, $CH_3$), 0.86 (t, J=7.5Hz, $CH_3$, minor), 0.94 (s, $CH_3$), 0.96 (s, $CH_3$, minor), 1.15 (m, $CH_3$, minor), 1.19 (d, J=10Hz, $CH_3$), 1.26 (d, J=10Hz, $CH_3$), 1.62 (s, $CH_3$), 1.78 (s, $CH_3$), 1.84 (s, $CH_3$, minor), 2.21 (m, $CH_2$), 2.29 (m, $CH_2$), 2.43 (m, $CH_2$ and CH), 2.57 (m, CH), 2.66 (ddd, $J_1=J_2=7.5Hz$, $J_3=20Hz$, $CH_2$), 2.76 (m, CH, minor), 2.9 (m, $CH_2$, minor), 3.01 (m, $CH_2$, minor) 3.07 (m, $CH_2$), 3.22 (m, $CH_2$), 3.36 (s, $OCH_3$), 3.4 (s, $OCH_3$), 3.42 (s, $OCH_3$), 3.43 (s, $OCH_3$, minor), 3.53 (m, CH), 3.67 (m, CH), 3.87 (CH, major and minor), 4.19 (d, J=15Hz, CH), 4.27 (ddd, $J_1=J_2=5Hz$, $J_3=15Hz$, CH, minor), 4.46 (m, m, CH), 4.56 (m, CH, minor), 4.69 (br d, J=20Hz, $CH_2$), 4.82 (m, CH), 5.08 (m, CH), 5.11 (m, CH), 5.13 (m, CH, minor), 5.33 (m, CH, minor), 5.35 (m, CH), 5.56 (m, CH, minor), 5.52 (s, benzyl$CH_2$), 5.77 (d, J=7.5 Hz, CH), 5.83 (d, J=7.5Hz, CH, minor), 7.63 (d, 2H, J=15Hz, ArCH), 9.0 (d, 2H, J=15Hz, ArCH);

Analysis calculated for $C_{51}H_{75}N_3O_{18}S$: C, 57.34; H, 7.26; N, 3.93. Found C, 57.52; H, 7.15;N,4.03.

EXAMPLE 12

(1R,9S,12S,13R,14S,17R,21S,23S,24R,25S,27R)-17-ethyl-1,14-dihydrox-12-(E)-2-[(1R,3R,4R)-4-({[({[(1R,2S,5R)-2-isopropyl-5-methylcyclohexyl]oxy}carbonyl)amino]sulfonyl}oxy)-3-methoxycyclohexyl]-1-methylethenyl}-23,25-dimethoxy-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting (1R,2S,5R) menthol for methanol.

MS (FAB) m/z: (M+H)$^+$=1091, M+K$^+$=1129;

$^{13}$C NMR (500 MHz in Pyridine-d$_5$) δ211.5 (q), 210.7 (q, minor), 199.6 (q, minor), 198.8 (q), 170.1 (q, minor), 170.0 (q), 167.3 (q, minor), 167.0 (q), 152.1 (q, minor, —NHCOO—), 139.4 (q, minor), 138.4 (q), 133.7 (q, minor), 133.3 (q), 131.9 (t), 130.7 (t, minor), 124.6 (t, minor), 124.5 (t), 99.7 (q, minor), 98.9 (q), 86.7 (t, minor), 86.6 (t), 80.8 (t, minor), 80.8 (t), 80.7 (t), 77.9 (t, minor), 76.7 (t, menthyl 1—CH), 76.2 (t), 74.8 (t, minor), 74.3 (t), 74.0 (t, minor), 73.1 (t), 69.7 (t), 68.9 (t, minor), 57.7 (t, menthyl 2—CH), 57.7 (p, minor), 57.5 (p), 57.5 (p), 57.0 (t), 56.2 (p), 55.9 (p, minor), 55.6 (t), 55.3 (t, minor), 53.0 (t, minor), 49.4 (s), 48.0 (s, minor), 47.9 (s), 47.5 (t, menthyl 5—CH), 46.5 (s, minor), 44.6 (s, minor), 41.4 (t), 41.3 (s, menthol ring, $CH_3$—CHCH$_2$—CHCOO), 41.1 (t, minor), 39.4 (s), 36.7 (s, minor), 36.7 (s), 35.9 (t), 35.5 (t, minor), 35.1 (s, minor), 34.5 (t), 33.1 (s), 31.5 (t, menthyl CH(CH$_3$)2), 30.9 (s, minor), 30.9 (s), 30.6 (s, minor), 30.5 (s), 28.2 (s), 27.6 (t, minor), 27.5 (s, minor), 26.6 (t), 26.4 (p), 25.2 (s, minor), 25.0 (s), 24.8 (s), 24.4 (s, minor), 23.7 (s, menthol 4—$CH_2$), 22.1 (s, menthyl group CH$_3$CHCH$_3$), 21.8 (s, minor), 21.5 (s), 20.9 (t, menthyl group CH$_3$CHCH$_3$), 20.6 (p, minor), 20.0 (p), 16.9 (p), 16.8 (p, minor), 16.6 (p,menthyl CH—CH$_3$), 16.3 (p), 16.0 (p), 13.7 (p, minor), 13.3 (p), 12.0 (p, minor), 11.9 (p), 10.8 (p), 10.5 (p, minor);

$^1$H NMR (500 MHz in Pyridine-d$_5$) δ0.82 (m, $CH_3$), 0.83, 0.86 and 0.88 (3xCH$_3$ mentholCH$_3$), 0.94 (s, $CH_3$), 0.96 (s, $CH_3$, minor), 1.15 (d, J=7.5Hz, $CH_3$, minor), 1.19 (d, J=7.5Hz, $CH_3$), 1.27 (d, J=7.5Hz, $CH_3$), 1.45 (m, menthy $CH_2$), 1.55 (m, menthyl$CH_2$), 1.61 (s, $CH_3$), 1.77 (s, $CH_3$), 1.83 (s, $CH_3$, minor), 2.21 (m, $CH_2$), 2.28 (m, $CH_2$), 2.43 (m, $CH_2$ and CH), 2.49 (m, 1H, menthyl CH), 2.55 (m, CH), 2.65 (ddd, $J_1=J_2=7.5Hz$, $J_3=15Hz$, $CH_2$), 2.75 (m, CH, minor), 2.88 (ddd, $J_1=J_2=7.5Hz$, $J_3=15Hz$, $CH_2$, minor), 3.01 (m, $CH_2$, minor), 3.05 (m, $CH_2$), 3.21 (m, $CH_2$), 3.41, 3.43, 3.55 (3s, $OCH_3$, $OCH_3$, $OCH_3$), 3.53 (m, CH), 3.67 (m, CH), 3.87 (CH, major and minor), 4.18 (d, J=10Hz, CH), 4.27 (m, CH, minor), 4.46 (m, m, CH), 4.55 (m, CH, minor), 4.69 (br d, J=10Hz, $CH_2$), 4.87 (m, 1H, menthyl CH), 4.94 (m, CH), 5.08 (m, CH), 5.11 (m, CH), 5.13 (m, CH, minor), 5.34 (m, CH, minor), 5.37 (m, CH), 5.50 (m, CH, minor), 5.78 (d, J=5Hz, CH), 5.83 (d, J=5Hz, CH, minor);

Analysis calculated for $C_{54}H_{88}N_2O_{16}S$: C, 61.57; H, 8.42; N, 2.65. Found C, 61.38; H, 8.52; N, 2.62.

EXAMPLE 13

(1R,9S,12S,13R,14S,17R,21S,23S,24R,25S,27R)-12-((E)-2-{(1R,3R,4R)-4-[({[(1-adamantylmethoxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene The title compound was prepared using the procedure described in Example 1 substituting 1-adamanthylmethanol alcohol for methanol.

MS (FAB) m/z: $(M+K)^+=1101$, $(M+2K-H)^+=1139$;

$^{13}$C NMR (500 MHz in Pyridine-$d_5$) δ211.5 (q), 210.7 (q, minor), 199.6 (q, minor), 198.8 (q), 170.1 (q, minor), 170.0 (q), 167.3 (q, minor), 167.0 (q), 152.6 (q, minor, —NHCOO—), 139.3 (q, minor), 138.4 (q), 133.6 (q, minor), 133.2 (q), 132.0 (t), 130.8 (t, minor), 124.6 (t, minor), 124.5 (t), 99.7 (q, minor), 98.9 (q), 86.3 (t, minor), 86.2 (t), 80.8 (t, minor), 80.7 (t), 80.6 (t), 79.5 (t, minor), 77.9 (t, minor), 76.2 (t), 76.0 (s, —CH$_2$COO), 74.8 (t, minor), 74.3 (t), 74.0 (t, minor), 73.1 (t), 69.6 (t), 68.8 (t, minor), 57.7 (p, minor), 57.5 (p), 57.4 (p), 57.0 (t), 56.1 (p), 55.8 (p, minor), 55.5 (t), 55.2 (t, minor), 53.0 (t, minor), 49.3 (s), 48.1 (s, minor), 47.9 (s), 46.5 (s, minor), 44.6 (s, minor), 41.4 (t), 41.0 (t, minor), 39.4 (s), 39.8 (s, minor), 39.2 (s, adamantyl 3xCH$_2$), 37.6 (s, minor), 37.0 (s, adamantyl 3xCH$_2$), 36.6 (s, minor), 36.6 (s), 35.9 (t), 35.5 (t, minor), 35.1 (s, minor), 34.5 (t), 33.1 (s), 31.0 (s, minor), 30.9 (s), 30.5 (s, minor), 30.5 (s), 28.8 (t, minor), 28.3 (t, Adamantyl 3xCH), 28.2 (s), 27.5 (t, minor), 27.5 (s, minor), 26.5 (t), 25.2 (s, minor), 25.0 (s), 24.8 (s), 24.4 (s, minor), 21.8 (s, minor), 21.5 (s), 20.6 (p, minor), 19.9 (p), 16.8 (p), 16.8 (p, minor), 16.3 (p, minor), 16.0 (p), 13.7 (p, minor), 13.3 (p), 11.9 (p, minor), 11.8 (p), 10.7 (p), 10.5 (p, minor);

$^1$H NMR (500 MHz in Pyridine-$d_5$) δ0.82 (t, J=7.5Hz, CH$_3$), 0.86 (t, J=7.5Hz, CH$_3$, minor), 0.94 (s, CH$_3$), 0.96 (s, CH$_3$, minor), 1.15 (d, J=7.5Hz, CH$_3$, minor), 1.19 (d, J=7.5Hz, CH$_3$), 1.26 (d, J=7.5Hz, CH$_3$), 1.54 (s, adamantylCH$_2$), 1.62 (s, CH$_3$), 1.78 (s, CH$_3$), 1.84 (s, CH$_3$, minor), 2.21 (m, CH$_2$), 2.29 (m, CH$_2$), 2.43 (m, CH$_2$ and CH), 2.57 (m, CH), 2.66 (ddd, J1=J2=7.5Hz, J3=15Hz, CH$_2$), 2.76 (m, CH, minor), 2.9 (ddd, J$_1$=J$_2$=7.5Hz, J$_3$=15Hz, CH$_2$, minor), 3.01 (m, CH$_2$, minor), 3.07 (ddd, J$_1$=J$_2$=7.5Hz, J$_3$=15Hz, CH$_2$), 3.22 (m, CH$_2$), 3.35 (d, 2H, OCH$_2$-adamantyl), 3.41 (s, OCH$_3$, minor), 3.415 (s, OCH$_3$), 3.42 (s, OCH$_3$), 3.43 (s, OCH$_3$), 3.53 (m, CH), 3.67 (m, CH), 3.87 (CH, major and minor), 4.19 (d, J=10Hz, CH), 4.27 (ddd, J$_1$=J$_2$=2.5Hz, J3=10Hz, CH, minor), 4.46 (m, CH), 4.56 (m, CH, minor), 4.69 (br d, J=15Hz, CH$_2$), 4.84 (m, CH), 5.08 (m, CH), 5.11 (m, CH), 5.13 (m, CH, minor), 5.33 (m, CH, minor), 5.35 (m, CH), 5.56 (m, CH, minor), 5.77 (d, J=5Hz, CH), 5.83 (d, J=5Hz, CH, minor);

Analysis calculated for $C_{55}H_{86}N_2O_{16}S$: C, 62.12; H, 8.15; N, 2.63. Found C, 61.80; H, 8.24; N, 2.31.

EXAMPLE 14

(1R,2R,4R)-4-1(E)-2-[(1R,9S,12S,13R,14S,17R,21S,23S,24R,25S,27R)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-en-12-yl]-1-propenyl}-2-methoxycyclohexylsulfamate The product from Example 4 (100 mg) was treated with 3 mL of 4N-HCl in dioxane for 15 minutes at room temperature. The solvent was removed and the crude product was purified by silica gel, eluting with 40 % acetone in hexane, and further purified by microsorb HPLC chromatography.

MS (FAB) m/z: $(M+K)^+=909$;

$^{13}$C NMR (500 MHz in Pyridine-$d_5$) δ211.6 (q), 210.8 (q, minor), 199.6 (q, minor), 198.8 (q), 170.1 (q, minor), 170.0 (q), 167.3 (q, minor), 167.0 (q), 139.4 (q, minor), 138.4 (q), 133.5 (q, minor), 133.2 (t), 132.2 (t), 131.0 (t, minor), 124.6 (t, minor), 124.5 (t), 99.7 (q, minor), 98.9 (q), 83.5 (t, minor), 83.4 (t), 81.1, 81.0 (t), 80.7 (t, minor), 79.5 (t, minor), 77.9 (t, minor), 76.3 (t), 74.8 (t, minor), 74.3 (t), 74.0 (t, minor), 73.1 (t), 69.7 (t), 69.0 (t, minor), 57.7 (p, minor), 57.5 (p), 57.4 (p), 57.1 (t), 56.2 (p), 55.9 (p, minor), 55.6 (t), 55.3 (t, minor), 53.0 (t, minor), 49.4 (s), 48.0 (s, minor), 47.9 (s), 46.5 (s, minor), 44.6 (s, minor), 41.4 (t), 41.1 (t, minor), 39.4 (s), 36.9 (s), 35.9 (t), 35.5 (t, minor), 35.1 (s, minor), 34.6 (t), 34.5 (s, minor), 33.1 (s), 32.9 (s, minor), 31.1 (s, minor), 31.1 (s), 30.7 (s, minor), 30.6 (s), 28.2 (s), 26.6 (t), 25.2 (s, minor), 25.0 (s), 24.9 (s), 24.4 (s, minor), 21.8 (s, minor), 21.5 (s), 20.6 (p, minor), 20.0 (p), 16.9 (p), 16.8 (p, minor), 16.3 (p, minor), 16.0 (p), 13.7 (p, minor), 13.4 (p), 12.0 (p, minor), 11.9 (p), 10.8 (p), 10.5 (p, minor);

$^1$H NMR (500 MHz in pyridine-$d_5$) δ0.82 (t, J=7.5Hz, CH$_3$), 0.87 (t, J=7.5Hz, CH$_3$, minor), 0.94 (s, CH$_3$), 0.96 (s, CH$_3$, minor), 1.15 (d, J=7.5Hz, CH$_3$, minor), 1.18 (d, J=7.5Hz, CH$_3$), 1.26 (d, J=7.5Hz, CH$_3$), 1.63 (s, CH$_3$), 1,79 (s, CH$_3$), 1.84 (s, CH$_3$, minor), 2.29 (m, CH$_2$), 2.55 (m, CH), 2.66 (d,d,d, J$_1$=J$_2$=7.5 Hz, J$_3$=15Hz, CH$_2$), 2.76 (m, CH, minor), 2.89 (d,d, d, J$_1$=J$_2$=7.5 Hz, J$_3$=15Hz, CH, minor), 3.0 (d, J=7.5 Hz, CH, minor), 2.66 (d,d ,d, J$_1$=J$_2$=7.5 Hz, J$_3$=15Hz, CH), 3.36 (s, OCH$_3$, minor), 3.40 (s, OCH$_3$), 3.42 (s, OCH$_3$), 3.44 (s, OCH$_3$), 3.53 (m, CH), 3.68 (m, CH), 3.87 (m, CH), 3.9 (m, CH, minor), 4.185 (d, J=10 Hz, CH), 4.27 (m, CH, minor), 4.47 (m, CH), 4.55 (m, CH, minor), 4.70 (m, CH$_2$), 5.10 (m, CH), 5.125 (m, CH), 5.35 (m, CH, minor), 5.38 (m, CH), 5.52 (br d, J=7.5Hz, CH, minor), 5.78 (d, J=5Hz, CH), 5.84 (d, J=5Hz, CH, minor).

Analysis calculated for $C_{43}H_{70}N_2O_{14}S$: C, 59.29; H, 8.09; N, 3.21. Found C, 59.02; H, 8.44; N, 3.18.

EXAMPLE 15

(1R,9S,12S,13R,14S,17R,21S,23S,24R,25S,27R)-17-ethyl-1,14-dihydroxy-23,25-dimethoxy-12-{(E)-2-[(1R,3R)-3-methoxy-4-oxocyclohexyl]-1-methylethenyl}-13,19,21,27-tetramethyl-11,28-dioxa-4-azatricyclo[22.3.1.0$^{4,9}$]octacos-18-ene-2,3,10,16-tetrone Methylsulfide-chlorine complex was prepared by adding oxalyl chloride (0.32 g) into a solution of dimethylsulfoxide (0.44 g) in 4 mL of methylene chloride and stirred at −70° C. for 30 minutes. The solution of the complex was slowly added to a stirred solution of ascomycin (1.6 g) in 5 mL of methylene chloride at −70° C. After stirring for 30 minutes, triethylamine (1.4 g) was added and the mixture was allowed to stir for an additional 30 minutes at −70° C. The reaction mixture was then allowed to warm to room temperature followed by additional stirring for 1 hour. The reaction mixture was diluted with 100 mL of ether, washed with 1N-HCl aq. solution (30 mL×2), brine (30 mL), dried over magnesium sulfate anhydrous, and the solvent removed in vacuo. The crude product was purified on 70 gram of silica gel, eluting with ether to obtain 0.95 g of the title compound.

MS (FAB) m/z: $(M+H)^+=790$.

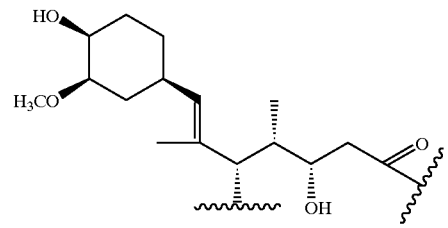

EXAMPLE 16

(1R,9S,12S,13R,14S,17R,21S,23S,24R,25S,27R)-17-ethyl-1,14-dihydroxy-12-{(E)-2-[(1R,3R,4S)-4-hydroxy-3-methoxycyclohexyl]-1-methylethenyl}-23,25-dimethoxy-13,19,21,27-tetramethyl-11,28-dioxa-4-azatricyclo[22.3.1.0$^{4,9}$]octacos-18-ene-2,3,10,16-tetrone Lithium tri-n-butoxyaluminum hydride (0.2 mL, 1M in THF) was slowly added to a stirred solution of the product from Example 15 (0.058 g) in 1 mL of anhydrous THF at −70° C. under a nitrogen atmosphere. After stirring at −70° C. for 3 hours, the mixture was partitioned between 50 mL of ether and 10 mL of 1N-HCl. The etheral solution was washed with brine, dried over magnesium sulfate anhydrous. The obtained crude product was purified by preparative TLC, using 35% acetone in hexane as a solvent to afford 0.025 g of the title compound.

MS (FAB) m/z: (M+K)$^+$=830.

Sulfamate analogs wherein R$^6$ is —OS(O)$_2$NHR$^9$, wherein R$^9$ is previously defined, can be prepared using the product from Example 16 and the procedures described in Examples 1–14.

We claim:

1. A compound according to formula I:

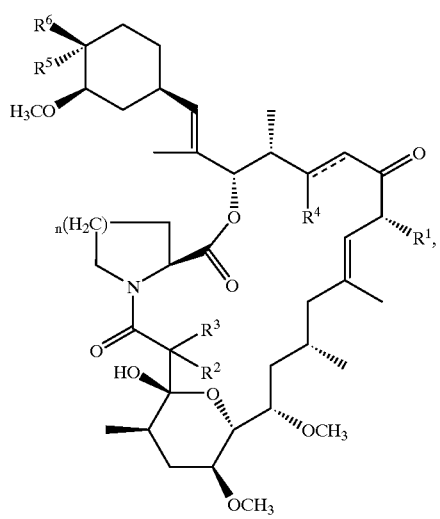

I or a pharmaceutically acceptable salt, ester, amide or prodrug thereof, wherein n is an integer of 1–3;

R$^1$ is selected from the group consisting of
(1) methyl,
(2) ethyl,
(3) propyl, and
(4) allyl;

R$^2$ and R$^3$ are independently selected from the group consisting of
(1) hydrogen and
(2) —OR$^7$, wherein R$^7$ is selected from the group consisting of
a) hydrogen and
b) hydroxy protecting group, or R$^2$ and R$^3$ taken together are selected from the group consisting of
(1) oxo and
(2) thioxo;

R$^4$ is selected from the group consisting of
(1) hydrogen and
(2) —OR$^7$, wherein R$^7$ is previously defined;

R$^5$ and R$^6$ are independently selected from the group consisting of
(1) hydrogen and
(2) —OS(O)$_2$NHR$^8$, wherein R$^8$ is selected from the group consisting of
(a) hydrogen and
(b) —C(O)OR$^9$, wherein R$^9$ is selected from the group consisting of
(i) alkyl,
(ii) aryl,
(iii) arylalkyl,
(iv) cycloalkyl,
(v) cycloalkylalkyl, and
(vi) heterocyclealkyl, provided that at least one of R$^5$ and R$^6$ is other than hydrogen; and a broken line represents the presence of an optional double bond, provided that when R$^4$ is —OR$^7$, wherein R$^7$ is hydrogen, the double bond is absent.

2. A compound according to claim 1 wherein,
R$^1$ is ethyl;
R$^2$ and R$^3$ taken together are oxo;
R$^4$ is —OR$^7$;
R$^7$ is hydrogen; and
the double bond is absent.

3. A compound according to claim 1 of formula II:

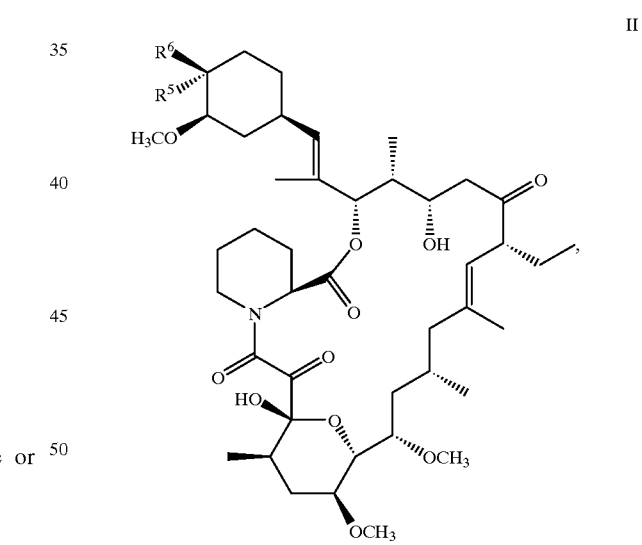

II or a pharmaceutically acceptable salt, ester, amide or prodrug thereof.

4. A compound according to claim 3 wherein,
R$^5$ is —OS(O)$_2$NHR$^8$; and
R$^8$ is hydrogen.

5. A compound according to claim 4 that is
(1R,2R,4R)-4-{(E)-2-[(1R,9S,12S,13R,14S,17R,21S,23S,24R,25S,27R)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-en-12-yl]-1-propenyl}-2-methoxycyclohexylsulfamate.

6. A compound according to claim 3 wherein, $R^5$ is —OS(O)$_2$NHR$^8$;

$R^8$ is —C(O)OR$^9$; and $R^9$ is alkyl.

7. A compound according to claim 6 that is selected from the group consisting of (1R,9S,12S,13R,14S,17R,21S,23S,24R,25S,27R)-17-ethyl-1,14-dihydroxy-23,25-dimethoxy-12-{(E)-2-[(1R,3R,4R)-3-methoxy-4-({[(methoxycarbonyl)amino]sulfonyl}oxy)cyclohexyl]-1-methylethenyl}-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-12-{(E)-2-[(1R,3R,4R)-4-({[(ethoxycarbonyl)amino]sulfonyl}oxy)-3-methoxycyclohexyl]-1-methylethenyl}-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene, and (1R,9S,12S,13R,14S,17R,2 1S,23S,24R,25S,27R)-12-{(E)-2-[(1R,3R,4R)-4-({[(tert-butoxycarbonyl)amino]sulfonyl}oxy)-3-methoxycyclohexyl]-1-methylethenyl}-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene.

8. A compound according to claim 3 wherein, $R^5$ is —OS(O)$_2$NHR$^8$;

$R^8$ is —C(O)OR$^9$; and $R^9$ is cycloalkyl.

9. A compound according to claim 8 that is selected from the group consisting of (1R,9S,12S,13R,14S,17R,21S,23S,24R,25S,27R)-12-((E)-2-{(1R,3R,4R)-4-[({[(cyclopentyloxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-12-((E)-2-{(1R,3R,4R)-4-[({[(cyclohexyloxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl- 2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-12-((E)-2-{(1R,3R,4R)-4-[({[(cycloheptyloxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene, and (1R,9S,12S,13R,14S,17R,21S,23S,24R,25S,27R)-17-ethyl-1,14-dihydroxy-12-{(E)-2-[(1R,3R,4R)-4-({[({[(1R,2S,5R)-2-isopropyl-5-methylcyclohexyl]oxy}carbonyl)amino]sulfonyl}oxy)-3-methoxycyclohexyl]-1-methylethenyl}-23,25-dimethoxy-13,19,21,27-tetramethyl-2,3,10,16-tetraoxo-11,28-dioxa-4-azatricyclo[22.3.1.0$^{4,9}$]octacos-18-ene.

10. A compound according to claim 3 wherein, $R^5$ is —OS(O)$_2$NHR$^8$;

$R^8$ is —C(O)OR$^9$; and $R^9$ is arylalkyl.

11. A compound according to claim 10 that is selected from the group consisting of (1R,9S,12S,13R,14S,17R,21S,23S,24R,25S,27R)-12-((E)-2-{(1R,3R,4R)-4-[({[(benzyloxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene and (1R,9S,12S,13R,14S,17R,21S,23S,24R,25S,27R)-17-ethyl-1,14-dihydroxy-23,25-dimethoxy-12-[(E)-2-((1R,3R,4R)-3-methoxy-4-{[({[(4-nitrobenzyl)oxy]carbonyl}amino)sulfonyl]oxy}cyclohexyl)-1-methylethenyl]-13,19,21,27-tetramethyl-2,3,10,16-tetraoxo-11,28-dioxa-4-azatricyclo[22.3.1.0$^{4,9}$]octacos-18-ene.

12. A compound according to claim 3 wherein, $R^5$ is —OS(O)$_2$NHR$^8$;

$R^8$ is —C(O)OR$^9$; and $R^9$ is heterocyclealkyl.

13. A compound according to claim 12 that is selected from the group consisting of (1R,9S,12S,13R,14S,17R,21S,23S,24R,25S,27R)-17-ethyl-1,14-dihydroxy-23,25-dimethoxy-12-((E)-2-{(1R,3R,4R)-3-methoxy-4-[({[(4-pyridinylmethoxy)carbonyl]amino}sulfonyl)oxy]cyclohexyl}-1-methylethenyl)-13,19,21,27-tetramethyl-2,3,10,16-tetraoxo-11,28-dioxa-4-azatricyclo[22.3.1.0$^{4,9}$]octacos-18-ene, (1R,9S,12S,13R,14S,17R,21S,23S,24R,25S,27R)-17-ethyl-1,14-dihydroxy-23,25-dimethoxy-12-((E)-2-{(1R,3R,4R)-3-methoxy-4-[({[(3-pyridinylmethoxy)carbonyl]amino}sulfonyl)oxy]cyclohexyl}-1-methylethenyl)-13,19,21,27-tetramethyl-2,3,10,16-tetraoxo-11,28-dioxa-4-azatricyclo[22.3.1.0$^{4,9}$]octacos-18-ene, and (1R,9S,12S,13R,14S,17R,21S,23S,24R,25S,27R)-17-ethyl-1,14-dihydroxy-23,25-dimethoxy-12-((E)-2-{(1R,3R,4R)-3-methoxy-4-[({[(2-pyridinylmethoxy)carbonyl]amino}sulfonyl)oxy]cyclohexyl}-1-methylethenyl)-13,19,21,27-tetramethyl-2,3,10,16-tetraoxo-11,28-dioxa-4-azatricyclo[22.3.1.0$^{4,9}$]octacos-18-ene.

14. A compound according to claim 3 wherein, $R^5$ is —OS(O)$_2$NHR$^8$;

$R^8$ is —C(O)OR$^9$; and $R^9$ is cycloalkylalkyl.

15. A compound according to claim 14 that is (1R,9S,12S,13R,14S,17R,21S,23S,24R,25S,27R)-12-((E)-2-{(1R,3R,4R)-4-[({[(1-adamantylmethoxy)carbonyl]amino}sulfonyl)oxy]-3-methoxycyclohexyl}-1-methylethenyl)-17-ethyl-1,14-dihydroxy-23,25-dimethoxy-13,19,21,27-tetramethyl-2,3,10,16-tetraoxo-11,28-dioxa-4-azatricyclo[22.3.1.0$^{4,9}$]octacos-18-ene.

16. A pharmaceutical composition useful for immunomodulation comprising a therapeutically effective amount of a compound of claim 1 in combination with a pharmaceutically acceptable carrier.

17. A method of suppressing the immune system in a host mammal in need of such treatment comprising administering a therapeutically effective amount of a compound of claim 1.

18. The method according to claim 17 wherein the method consists of treating autoimmune diseases.

19. The method according to claim 18 wherein the autoimmune disease comprises psoriasis, atopical dermatitis, contact dermatitis and further eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, acne and alopecia areata.